(12) United States Patent
Bennett et al.

(10) Patent No.: US 11,344,726 B2
(45) Date of Patent: May 31, 2022

(54) SYSTEMS AND METHODS FOR THE TREATMENT OF PAIN THROUGH NEURAL FIBER STIMULATION

(71) Applicant: SPR Therapeutics, Inc., Cleveland, OH (US)

(72) Inventors: Maria E. Bennett, Beachwood, OH (US); Joseph W. Boggs, Chapel Hill, NC (US); Warren M. Grill, Chapel Hill, NC (US); John Chae, Strongsville, OH (US)

(73) Assignee: SPR Therapeutics, Inc., Cleveland, OH (US)

( * ) Notice: Subject to any disclaimer, the term of this patent is extended or adjusted under 35 U.S.C. 154(b) by 223 days.

(21) Appl. No.: 16/529,076

(22) Filed: Aug. 1, 2019

(65) Prior Publication Data

US 2019/0351232 A1 Nov. 21, 2019

Related U.S. Application Data

(63) Continuation of application No. 15/854,206, filed on Dec. 26, 2017, now Pat. No. 10,722,715, which is a
(Continued)

(51) Int. Cl.
*A61N 1/36* (2006.01)

(52) U.S. Cl.
CPC ..... *A61N 1/36071* (2013.01); *A61N 1/36003* (2013.01); *A61N 1/36017* (2013.01); *A61N 1/36021* (2013.01); *A61N 1/36057* (2013.01)

(58) Field of Classification Search
CPC .................. A61N 1/36071; A61N 1/36003
(Continued)

(56) References Cited

U.S. PATENT DOCUMENTS 2,521,722 A 9/1950 Hubbell et al.
3,067,401 A 12/1962 Rhodes
(Continued)

FOREIGN PATENT DOCUMENTS

GB 0945482 1/1964
GB 2085733 5/1982
(Continued)

OTHER PUBLICATIONS

J J Wall MD, Axillary Nerve Blocks, Am Fam Physician, vol. 11, No. 5, 135-142, May 1975.
(Continued)

*Primary Examiner* — Nadia A Mahmood
(74) *Attorney, Agent, or Firm* — McDonald Hopkins LLC

(57) ABSTRACT

Embodiments of the present invention provide systems and methods for the treatment of pain through activation of select neural fibers. The neural fibers may comprise one or more afferent neural fibers and/or one or more efferent neural fibers. If afferent fibers are stimulated, alone or in combination with efferent fibers, a therapeutically effective amount of electrical stimulation is applied to activate afferent pathways in a manner approximating natural afferent activity. The afferent fibers may be associated with primary receptors of muscle spindles, golgi tendon organs, secondary receptors of muscle spindles, joint receptors, touch receptors, and other types of mechanoreceptors and/or proprioceptors. If efferent fibers are stimulated, alone or in combination with afferent fibers, a therapeutically effective amount of electrical stimulation is applied to activate intrafusal and/or extrafusal muscle fibers, which results in an indirect activation of afferent fibers associated therewith.

15 Claims, 7 Drawing Sheets

Related U.S. Application Data continuation of application No. 15/453,978, filed on Mar. 9, 2017, now Pat. No. 9,855,427, which is a continuation of application No. 14/336,633, filed on Jul. 21, 2014, now Pat. No. 9,616,229, which is a continuation of application No. 13/309,024, filed on Dec. 1, 2011, now Pat. No. 8,788,046, which is a continuation-in-part of application No. 13/294,875, filed on Nov. 11, 2011, now Pat. No. 10,668,285.

(60) Provisional application No. 61/418,801, filed on Dec. 1, 2010, provisional application No. 61/418,768, filed on Dec. 1, 2010, provisional application No. 61/412,685, filed on Nov. 11, 2010.

(58) Field of Classification Search
USPC .......................................................... 607/46
See application file for complete search history.

(56) References Cited

U.S. PATENT DOCUMENTS

| | | |
|---|---|---|
| 3,568,675 A | 3/1971 | Harvey |
| 3,663,965 A | 4/1972 | Lee, Jr. et al. |
| 3,701,080 A | 10/1972 | Baisz et al. |
| 3,850,161 A | 11/1974 | Liss |
| 3,964,470 A | 6/1976 | Trombley |
| 4,019,518 A | 4/1977 | Maurer et al. |
| 4,026,301 A | 5/1977 | Friedman et al. |
| 4,144,889 A | 3/1979 | Tyers et al. |
| 4,223,679 A | 9/1980 | Schulman et al. |
| 4,250,882 A | 2/1981 | Adair |
| 4,281,660 A | 8/1981 | Fujiwara |
| 4,281,664 A | 8/1981 | Duggan |
| 4,326,534 A | 4/1982 | Axelgaard et al. |
| 4,408,608 A | 10/1983 | Daly et al. |
| 4,409,994 A | 10/1983 | Doring |
| 4,413,314 A | 11/1983 | Slater et al. |
| 4,453,162 A | 6/1984 | Money et al. |
| 4,459,989 A | 7/1984 | Borkan |
| 4,528,984 A | 7/1985 | Morawetz et al. |
| 4,528,987 A | 7/1985 | Slocum |
| 4,532,932 A | 8/1985 | Batty, Jr. |
| 4,558,704 A | 12/1985 | Petrofsky |
| 4,561,443 A | 12/1985 | Hogrefe et al. |
| 4,561,445 A | 12/1985 | Berke et al. |
| 4,569,352 A | 2/1986 | Petrofsky et al. |
| 4,579,120 A | 4/1986 | MacGregor |
| 4,586,510 A | 5/1986 | Glaser et al. |
| 4,595,010 A | 6/1986 | Radke |
| 4,622,973 A | 11/1986 | Agrawala |
| 4,632,116 A | 12/1986 | Rosen et al. |
| 4,639,667 A | 1/1987 | Andressen |
| 4,640,983 A | 2/1987 | Comte |
| 4,645,504 A | 2/1987 | Byers |
| 4,690,145 A | 9/1987 | King-Smith et al. |
| 4,693,254 A | 9/1987 | Mickiewicz et al. |
| 4,699,143 A | 10/1987 | Dufresne et al. |
| 4,793,353 A | 12/1988 | Borkan |
| 4,942,514 A | 7/1990 | Miyagaki et al. |
| 4,990,258 A | 2/1991 | Bjare et al. |
| 5,036,862 A | 8/1991 | Pohndorf |
| 5,063,929 A | 11/1991 | Bartelt et al. |
| 5,067,495 A | 11/1991 | Brehm |
| 5,167,229 A | 12/1992 | Peckham et al. |
| 5,247,434 A | 9/1993 | Peterson et al. |
| 5,285,781 A | 2/1994 | Brodard |
| 5,300,096 A | 4/1994 | Hall et al. |
| 5,330,515 A | 7/1994 | Rutecki et al. |
| 5,571,162 A | 11/1996 | Lin |
| 5,581,687 A | 12/1996 | Lyle et al. |
| 5,609,770 A | 3/1997 | Zimmerman et al. |
| 5,653,887 A | 8/1997 | Wahl et al. |
| 5,702,428 A | 12/1997 | Tippey et al. |
| 5,776,178 A | 7/1998 | Pohndorf et al. |
| 5,792,187 A | 8/1998 | Adams |
| 5,800,458 A | 9/1998 | Wingrove |
| 5,830,151 A | 11/1998 | Hadzic et al. |
| 5,836,995 A | 11/1998 | McGraw et al. |
| 5,861,017 A | 1/1999 | Smith et al. |
| 5,871,532 A | 2/1999 | Schroeppel |
| 5,873,900 A | 2/1999 | Maurer et al. |
| 5,948,007 A | 9/1999 | Starkebaum |
| 5,983,140 A | 11/1999 | Smith et al. |
| RE36,690 E | 5/2000 | McGraw et al. |
| 6,058,938 A | 5/2000 | Chu et al. |
| 6,104,957 A | 8/2000 | Alo |
| 6,167,304 A | 12/2000 | Loos |
| 6,355,025 B1 | 3/2002 | Phipps et al. |
| 6,381,496 B1 | 4/2002 | Meadows et al. |
| 6,440,094 B1 | 8/2002 | Maas |
| 6,454,758 B1 | 9/2002 | Thompson et al. |
| 6,461,357 B1 | 10/2002 | Sharkey et al. |
| 6,530,954 B1 | 3/2003 | Eckmiller |
| 6,600,954 B2 | 7/2003 | Cohen et al. |
| 6,609,031 B1 | 8/2003 | Law et al. |
| 6,613,014 B1 | 9/2003 | Chi |
| 6,671,544 B2 | 12/2003 | Baudino |
| 6,735,475 B1 | 5/2004 | Whitehurst et al. |
| 6,821,154 B1 | 11/2004 | Canfield et al. |
| 6,845,271 B2 | 1/2005 | Fang et al. |
| 7,079,882 B1 | 7/2006 | Schmidt |
| 7,187,982 B2 | 3/2007 | Seifert et al. |
| 7,239,918 B2 | 7/2007 | Strother et al. |
| 7,242,983 B2 | 7/2007 | Frei et al. |
| 7,302,296 B1 | 11/2007 | Hoffer |
| 7,324,853 B2 | 1/2008 | Ayal et al. |
| 7,337,005 B2 | 2/2008 | Kim et al. |
| 7,359,751 B1 | 4/2008 | Erickson et al. |
| 7,369,894 B2 | 5/2008 | Gerber |
| 7,373,204 B2 | 5/2008 | Gelfand et al. |
| 7,562,188 B2 | 7/2009 | Cavallo |
| 7,613,519 B2 | 11/2009 | De Ridder |
| 7,720,548 B2 | 5/2010 | King |
| 7,761,166 B2 | 7/2010 | Giftakis et al. |
| 7,792,591 B2 | 9/2010 | Rooney et al. |
| 7,810,571 B2 | 10/2010 | Beall |
| 7,848,821 B1 | 12/2010 | Ryu et al. |
| 7,945,330 B2 | 5/2011 | Gliner et al. |
| 7,949,395 B2 | 5/2011 | Kuzma |
| 8,103,341 B2 | 1/2012 | Libbus et al. |
| 8,204,607 B2 | 6/2012 | Rooney |
| 8,239,029 B2 | 8/2012 | Ridder |
| 8,249,713 B2 | 8/2012 | Fang et al. |
| 8,313,339 B2 | 11/2012 | Monier |
| 8,463,383 B2 | 6/2013 | Sakai et al. |
| 8,626,302 B2 | 1/2014 | Bennett et al. |
| 8,644,941 B2 | 2/2014 | Chu et al. |
| 8,700,177 B2 | 4/2014 | Strother et al. |
| 8,788,046 B2 | 7/2014 | Bennett |
| 8,788,047 B2 | 7/2014 | Bennett |
| 8,788,048 B2 | 7/2014 | Bennett |
| 8,886,337 B2 | 11/2014 | Bennett et al. |
| 8,954,153 B2 | 2/2015 | Boggs et al. |
| 8,965,516 B2 | 2/2015 | Bennett |
| 9,381,343 B2 | 7/2016 | Bennett et al. |
| 2001/0018606 A1 | 8/2001 | Ingle |
| 2002/0068930 A1 | 6/2002 | Tasto et al. |
| 2002/0099419 A1 | 7/2002 | Cohen et al. |
| 2003/0078633 A1 | 4/2003 | Firlik et al. |
| 2003/0100933 A1 | 5/2003 | Ayal et al. |
| 2003/0130706 A1 | 7/2003 | Douglas |
| 2003/0225361 A1 | 12/2003 | Sabra |
| 2003/0229360 A1 | 12/2003 | Gayton |
| 2004/0015204 A1 | 1/2004 | Whitehurst et al. |
| 2004/0122482 A1 | 6/2004 | Tang et al. |
| 2004/0186532 A1 | 9/2004 | Tadlock |
| 2004/0260312 A1 | 12/2004 | Magnusson et al. |
| 2005/0010259 A1 | 1/2005 | Gerber |
| 2005/0105201 A1 | 5/2005 | Christie, Jr. et al. |
| 2005/0143789 A1 | 6/2005 | Whitehurst et al. |
| 2005/0149154 A1 | 7/2005 | Cohen et al. |
| 2005/0182469 A1 | 8/2005 | Hunter |
| 2005/0240243 A1 | 10/2005 | Barolet et al. |

(56) References Cited

U.S. PATENT DOCUMENTS

| | | |
|---|---|---|
| 2005/0246006 A1 | 11/2005 | Daniels |
| 2006/0052828 A1* | 3/2006 | Kim ................. A61M 5/142 607/3 |
| 2006/0069415 A1 | 3/2006 | Cameron et al. |
| 2006/0095088 A1 | 5/2006 | De Ridder |
| 2006/0173507 A1 | 8/2006 | Mrva et al. |
| 2006/0195170 A1 | 8/2006 | Cohen |
| 2006/0206166 A1 | 9/2006 | Weiner |
| 2007/0021786 A1 | 1/2007 | Parnis et al. |
| 2007/0021803 A1 | 1/2007 | Deem et al. |
| 2007/0027501 A1 | 2/2007 | Jenson et al. |
| 2007/0027514 A1 | 2/2007 | Gerber |
| 2007/0072256 A1 | 3/2007 | Rooney et al. |
| 2007/0073356 A1 | 3/2007 | Rooney et al. |
| 2007/0073357 A1 | 3/2007 | Rooney et al. |
| 2007/0150034 A1 | 6/2007 | Rooney et al. |
| 2007/0213771 A1 | 9/2007 | Spinner |
| 2007/0219547 A1 | 9/2007 | Osypka |
| 2007/0244522 A1 | 10/2007 | Overstreet |
| 2007/0255340 A1 | 11/2007 | Giftakis et al. |
| 2007/0255365 A1 | 11/2007 | Gerber et al. |
| 2007/0255368 A1 | 11/2007 | Bonde et al. |
| 2008/0033511 A1 | 2/2008 | Dobak |
| 2008/0065171 A1 | 3/2008 | Fang et al. |
| 2008/0132982 A1 | 6/2008 | Gerber et al. |
| 2008/0228241 A1 | 9/2008 | Sachs |
| 2009/0099439 A1 | 4/2009 | Barolat |
| 2009/0192567 A1 | 7/2009 | Armstrong et al. |
| 2009/0221928 A1 | 9/2009 | Einav et al. |
| 2009/0281594 A1 | 11/2009 | King et al. |
| 2009/0326613 A1 | 12/2009 | Knoblich |
| 2010/0030300 A1 | 2/2010 | Feler et al. |
| 2010/0036280 A1 | 2/2010 | Ballegaard et al. |
| 2010/0036445 A1 | 2/2010 | Sakai et al. |
| 2010/0036454 A1 | 2/2010 | Bennett et al. |
| 2010/0082087 A1 | 4/2010 | Silipo et al. |
| 2010/0152808 A1 | 6/2010 | Boggs, II |
| 2010/0152809 A1 | 6/2010 | Boggs et al. |
| 2010/0280576 A1 | 11/2010 | Gerber et al. |
| 2010/0331883 A1 | 12/2010 | Schmitz |
| 2011/0021943 A1 | 1/2011 | Lacour et al. |
| 2011/0022114 A1 | 1/2011 | Navarro |
| 2011/0054565 A1 | 3/2011 | Wacnik et al. |
| 2011/0106207 A1 | 5/2011 | Cauller et al. |
| 2011/0208266 A1 | 8/2011 | Minogue et al. |
| 2011/0213221 A1 | 9/2011 | Roche |
| 2011/0224665 A1 | 9/2011 | Crosby et al. |
| 2011/0301670 A1 | 12/2011 | Gross et al. |
| 2012/0016439 A1 | 1/2012 | Alataris et al. |
| 2012/0035685 A1 | 2/2012 | Saha et al. |
| 2012/0197388 A1 | 8/2012 | Khairkhahan et al. |
| 2012/0232615 A1 | 9/2012 | Barolat |
| 2012/0271391 A1 | 10/2012 | Barolat |
| 2012/0290055 A1 | 11/2012 | Boggs, II |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2013/0013041 A1 | 1/2013 | Glukhovsky et al. |
| 2013/0066393 A1 | 3/2013 | Gross et al. |
| 2013/0096641 A1 | 4/2013 | Strother |
| 2013/0110196 A1 | 5/2013 | Alataris |
| 2013/0197615 A1 | 8/2013 | Rundle |
| 2013/0238066 A1 | 9/2013 | Boggs, II et al. |
| 2013/0296966 A1 | 11/2013 | Wongsampigoon et al. |
| 2014/0046416 A1 | 2/2014 | Bennett et al. |
| 2014/0107747 A1 | 4/2014 | Rooney et al. |
| 2014/0114374 A1 | 4/2014 | Rooney et al. |
| 2014/0288616 A1 | 9/2014 | Rawat et al. |
| 2014/0330339 A1 | 11/2014 | Bennett et al. |
| 2015/0182749 A1 | 7/2015 | Fang |
| 2015/0224251 A1 | 8/2015 | Rooney |

FOREIGN PATENT DOCUMENTS

| | | |
|---|---|---|
| GB | 2123698 | 2/1984 |
| GB | 2223949 | 4/1990 |
| GB | 2423020 | 8/2006 |
| WO | 2005105201 | 11/2005 |
| WO | 2006057734 | 6/2006 |
| WO | 2007136726 | 11/2007 |
| WO | 2010014260 | 2/2010 |
| WO | 2010044880 | 4/2010 |
| WO | 2012075265 | 6/2012 |
| WO | 2012075281 | 6/2012 |
| WO | 2012075299 | 6/2012 |
| WO | 2012075497 | 6/2012 |
| WO | 2013036630 | 3/2013 |
| WO | 2014099423 | 6/2014 |

OTHER PUBLICATIONS

Hansen, "EMG Controlled Functional . . . of the Paretic Hand", Scan. J. Rehab Med. Nov. 1979, pp. 189-193.

Ware et al., The MOS 36-!tem Short-Form Health Survey (SF-36) I Conceptual Framework and Item Selection, Medical Care, vol. 30 No 6, 473-483, Jun. 1992.

Prochazka et al., "Remote Monitoring . . . in Unrestrained Cats", Electroencephalogrphy & Clin. Neurophysiology, vol. 37, No. 6, Dec. 1974; pp. 649-653.

NeuroControl St!M (TM) System Brochure; circa Jan. 2000.

Gustafsson et al., A programme of static positional stretches does not reduce hemiplegic shoulder pain or maintain . . . , Clinical Rehabil, 20, 277-286, 2006.

Hurd et al., Shoulder Sling for Hemiplegia: Friend or Foe?, Arch Phys Med Rehabil, vol. 55, pp. 519-522, Nov. 1974.

Van der Windt et al., Review The efficacy of non-steroidal anti-inflammatory drugs (NSAIDS) for shoulder complaints . . . , J Clin Epidermiol, vol. 48, No. 5, 691-704, 1995.

Van Ouwenaller et al., Painful shoulder in hemiplegia, Arch Phys Med Rehabil, vol. 67, 23-26, Jan. 1986.

Turner-Stokes et aL, Shoulder pain after stroke: a review of the evidence base to inform the development of an integrated care pathway, Clinical Rehabil, 16, 276-298, 2002.

Teasell et al., Evidence-based review of stroke rehabilitation Appendix: Management of Post Stroke Pain, 10th Ed, 1-37, 2003.

Leob et al., "Design and Fabrication for Experimental Cochlear Prosti1esis", Med & Biomed Eng. & Comput. May 1983, pp. 241-253.

Krainick et aL, Pain reduction in amputees by long-term spinal cord stimulation, J Neurosurg, 52, pp. 346-350, 1980.

Kilgore et al., Synti1esis of Hand Grasp Using Functional Neuromuscular Stimulation, IEEE Trans Biomed Eng, 36(7), pp. 761-770, Jul. 1989.

Buckett et al., "A Microprocessor Based Portable Functional Electrical Stimulation System", Annual Conference on Rehabilitation Eng., San Diego, CA 198i, pp. 72-74.

Spincemaille et al, Technical data and complications of spinal cord stimulation: data from a randomized trial on critical limb . . . , Stereotact Funct Neurosurg 74, 63-72, 2000.

Goldman et al., Dorsal Genital Nerve Stimulation for the Treatment of Overactive Bladder Symptoms, Neurourology and Urodynamics, 27(6), pp. 499-503, 2008.

Thrope et al., "A Proportional Joystick Controller for High Level Quadriplegics", RESNA 8th Annual Conference, Memphis, TN 1985, pp. 401-403.

Snels et al., Treatment of hemiplegic shoulder pain in the Netherlands: results of a national survey, Clinical Rehabilitation, 14, 20-27, 2000.

Widar et al., Healti1-related quality of life in persons witi1 long-term pain after a stroke, J of Clinical Nursing, 13, 497-505, 2004.

Peckham et al., "Restoration of Hand Function in the Quadriplegic Through Electrical Stimulation", Functional Electrical Stimulation, Hanbrecht & Reswick, 1977, pp. 83-95.

(56) References Cited

OTHER PUBLICATIONS

Smith et al., "A Portable Microprocessor Controlled Implantable Functional Neuromuscular Stimulation System", Proceedings of tl1e 2nd Int. Cont. on Rellab, Eng. 1984.

Zorowitz et al., Shoulder Pain and Subluxation after stroke: Correlation or Coincidence?, The American Journal of Occupational Therapy, Vo! 50, No. 3, 194-201, Mar. 1996.

Yu et al, Comparing stimulation-induced pain during percutaneous (Intrarnuscu!ar) and transcutaneous neurornuscu!ar . . . , Arch Phys Med Rehabii, vol. 82, 756-760, Jun. 2001.

Yu et al., Percutaneous intramuscular neuromuscular electric stimulation for the treatment of shoulder subluxation and pain . . . , Arch Phys Med Rehabii, vol. 82, 20-25, Jan. 2001.

Peckham et al., Coordinated Two Mode Grasp in the Quadriplegic Initiated by Functional Neuromuscular Stimulation, IFAC Control Aspects of Prosthetics and Orthotics, 1982.

Yu et al, Case Report A Neuroprosthesis for high tetraplegia, The J of Spinal Cord Medicine, Vo! 24, No. 2, 109-113, Summer 2001.

Finsen et al., Transcutaneous Electrical Nerve Stimulation after Major Amputation, The Journal of Bone and Joint Surgery, vol. 70-B, No. 1, pp. 109-112 Jan. 1988.

Chae et al., Intramuscular Electrical Stimulation for Hemiplegic Shoulder Pain, Arn. J. Phys. Med, Rehabil., vol. 84, No. 11, pp. 832-842, Nov. 2005.

Chantraine et al., Should Pain and Dysfunction in Hemiplegia: Effects of Functional Electrical Stimulation, arch Phys Med Rehabil vol. 80, pp. 328-331, Mar. 1999.

Yu et aL, Intramuscular neuromusculai-electric stimulation for poststroke shoulder pain: A Mult!center randomized . . . , Arch Phys Med Rehabil, vol. 85 695-704, May 2004.

Gamble et al., Post stroke shoulder pain: more common than previously realized, European J of Pain, 4, pp. 313-315, 2000.

Giiffin et aL, Strapping the hemiplegic shoulder prevents development of pain during rehabilitation: a randomized controlled trial, Clinical Rehabil, 20, 287-295, 2006.

Gamble et al, Poststroke shoulder pain: a prospective study of the association and risk factors in 152 patients . . . , European J of Pain, 6, pp. 467-474, 2002.

International Search Report for PCT/US12/53952 dated Nov. 15, 2012.

European Patent Office, Extended European Search Report for Application 13760774.3, PCT/US2013/032627, dated Jan. 5, 2016, 11 pgs., European Patent Office, Germany.

Paeslack et al., "Design and Control of a Manipulator for Tetraplegics", Mechanism & Machine Theory, 1977, vol. 12, No. 5, pp. 413-423.

International Search Report and Written Opinion dated Feb. 3, 2010 in International Application Serial No. PCT/US2009/006414.

International Search Report and Written Opinion; PCT/US09/06403; dated Feb. 23, 2010.

Patent Cooperation Treaty (PCT), International Search Report and Written Opinion for Application PCT/US2011/062857 filed Dec. 1, 2011, dated Mar. 9, 2012, International Search Authority, US.

"Long Head of the Biceps Tendon Pain: Differential Diagnosis and Treatment" by Krupp et al. Published: Journal of Orthopaedic & Sports Physical Therapy, 2009 vol. 39 Issue:2 pp. SS-70 DOI: 10.2519/jospt.2009.2802 available at: http://www .jospt.org /doi/full/10.2519/jospt.2009.2802?code=jospt-site.

"Shoulder impingement syndrome" by Baffes et al., published Jul. 1998, available at http: //www.qooqle.ca/url?sa=t&rct=j&g=&esrc=s&source=web&cd=1&ved=OahUKEwi 85tj L6rLZAhUB2oMKHcZvDuoQFqqnMAA&url=http%3A%2F%2Fftp.uws.edu%2Fmain.html %3Fdownload%26weblink%30338e50fd65e877c83eaaf65d11aa8aa4%26realfilename%3DShoulderImpingementSyndrome.pdf&usq=AOvVaw1qpu5FORrnCz1Qj5AwSSw-.

Therapeutic effect of pulsed electromagnetic field in conservative treatment of subacromial impingement syndrome by Aktas et al., Aug. 2007 (Aug. 2007). Available at https://www.ncbi.nlm.nih.gov/pubmed/17086382.

International Search Report and the Written Opinion of the International Searching Authority, PCT/US2012/53952, SPR Therapeutics, LLC, dated Nov. 15, 2012.

International Search Report and the Written Opinion of the International Searching Authority, PCT/US2013/73647, SPR Therapeutics, LLC, dated Feb. 20, 2014.

Extended European Search Report for Application EP13866258.0 PCT/US2013073647, dated Sep. 5, 2016, European Patent Office, Germany.

Peckham et aL, "Multichannel Implantable Stimulator for Control of Paralyzed Muscle", IEEE Trans on Biomed. Eng. V. BME.

Buckett et al., "Shoulder Position Control, An Alternative Control Technique for Motion Impaired Individuals", Proceed of Int'i Conf, on Rehab. Eng., Toronto 1980, pp. 224-247.

Gybeis et aL, The Treatment of Pain Due to Peripheral Nerve Injury by Electrical Stirnuiation of the Injured Nerve, Advances in Pain Research & Therapy, vol. 13, 217-222, 1990.

Patent Cooperation Treaty (PCT), International Search Report and Written Opinion for Application PCT/US16/57267, dated Mar. 24, 2017, 43 pp., International Searching Authority, US.

International Preliminary Report on Patentability, NDI Medical, LLC, PCT/US2009/06414, dated Jan. 7, 2011.

International Search Report and the Written Opinion of the International Searching Authority, NDI Medical, LLC, PCT/US2009/06403, dated Feb. 23, 2010.

Forster, "Theoretical Design & Implementation of a Transcutaneous. Multichannei Stimulator for Neural Prosthesis Applications", J. Biomed Eng Voi 3, No. 2, Apr. 1981; pp. 107-120.

Vodovnik et al., "Electronic Detours of Broken Nerve Paths", Electronics, Sep. 20, 1965; pp. 110-116.

International Search Report and Written Opinion dated Mar. 15, 2012 in International Patent Application Serial No. PCT/US11/62882.

International Search Report and Written Opinion dated Mar. 9, 2012 in International Patent Application Serial No. PCT/US2011/062857.

International Preliminary Report on Patentabi!ity dated Dec. 6, 2012 from PCT application PCT/US11/62906 filed Dec. 1, 2011.

International Search Report and Written Opinion dated Mar. 30, 2012 in International Patent Application Serial No. PCT/US2011/062906.

International Search Report and Written Opinion dated Oct. 27, 2017 in International Patent Application Serial No. PCT/US2017/048904.

Maass et al., "Mobility Aid for Quadriplegics", Carnahan Conference on Electronic Prosthesis, Lexington, KY, Sep. 19-21, 1973; pJS 123-125.

European Patent Office, Extended European Search Report for application EP13758002.3 PCT/US2013030029, dated Sep. 9, 2015, 9 pgs., European Patent Office, Germany.

Rebersek et aL, "Proportionally Controlled Functional Electrical Stimulation of the Hand", Arch Phys Med Rehab. vol. 54, Aug. 1973, pp. 378-382.

Thrope et aL, "A Computer Controlled . . . Functional Neuromuscular Stimulation", IEEE Transactions on Bio Eng. vol. BME-32, No. 6, Jun. 1985, pp. 363-370.

Peckham et al., "Controlled Prehension and Release . . . Forearm Musculature", Annals of Biomedical Engineering, 1980, vol. 8, pp. 368-388.

Peckham et aL, "Restoration of Key Grip . . . Electrical Stimulation", Proceedings of Intern. Cont on Rehab. Eng., Toronto Canada, 1980, pp. 227-229.

Peckham et al., "Alteration in the Force . . . Electrical Stimulation", Clinical Orthopaedics & Related Research, No. 114, Jan.-Feb. 1976, pp. 326-344.

Crago, "Control of Movements by Functional Neuromuscular Stimulation", Eng. in Med & BioL Magazine, Sep. 1983, pp. 32-36.

Crago et al., "Closed Loop Control . . . Stimulation of Muscle", IEEE Transactions on Bio Eng., vol. MBE-27, No. 6, Jun. 1980, pp. 306-312.

Poon et al., "An Implantable RF-Powered Dual Channel Stimulator", Biotelemetry Patient Monitoring, vol. 8 No. 3, pp. 180-188 (1981).

(56) References Cited

OTHER PUBLICATIONS

Green et al., Systematic review of randomised controlled trials of interventions for painful shoulder: . . . , BMJ vol. 316 pp. 354-359, Jan. 31, 1998.
Chae et aL., Neuromuscular Stimulation for Upper Extremity Motor and Functional Recovery in Acute Hemiplegia, Stroke, 29,, 975-979, 1998.
Caldwell et al., A Percutaneous Wire Electrode for Chronic Research Use, IEEE Transactions on Biomedical Engineering, pp. 429-432, Sep. 1975.
Brooke et al., Shoulder Subluxation in Hemiplegia: Effects of Three Different Supports, Arch Phys Med Regahil vol. 72, Jul. 1991.
Bohannon et al., Shoulder Pain in Hemiplegia: Statistical Relationship with Five Variables, Arch Phys Med Rehabil, vol. 67, Aug. 1986.
Bigeleisen et al., Extraneural versus Intraneural Stimulation Thresholds during Ultrasound-guided Supraclavicular Block, Anesthesiology, 110, 1235-43, 2009.
Bhakta et al., Use of botulinum toxin in stroke patients with severe upper limb spasticity, Journal of Neuroloy, Neurosurgery, and Psychiatry, 61, 30-35, 1996.
Bhadra et al., Extraction Forces and Tissue Changes During Explant of CWRU-Type Intramuscular Electrodes from Rat Gastrocnernius, Annals of Biomed Eng, vol. 25, 1017-1025, 1997.
Bernstein et al., Spinal Cord Stimulation in Conjunction with Peripheral Nerve Field Stimulation . . . , Neummodulation Technology at the Neural Interface, vol. 1 1 No. 2 2008.
Bates et al., Veterans Affairs/Dept of Defense Clinical Practice Guideline for tile Management of Adult Stroke Rehabilitation Care. Stroke, pp. 2049-2056 Sep. 2005.
Krainick et al, Spinal Cord Stimulation in Postamputation Pain, Surg Neural, 4 (1), pp. 167-170, Jul. 1975.
Snels et al., Effect of triamcinolone acetonide injections on hemiplegic siloulder pain A randomized clinical trial, Stroke, 2396-2401, Oct. 2000.
Sheffler et al., Neuromuscular electrical stimulation in neurorehabilitation, Muscle and Nerve, pp. 562-590, May 2007.
Sharan et al., Evolving patterns of spinal cord stimulation in patients implanted with intractable low back and leg pain, Neuromodulation, vol. 5, No. 3, 167-179, 2002.
Sator-Katzenschlager et al., Subcutaneous Target Stimulation (STS) in chronic noncancer pain . . . , Pain Practice, vol. 10, Issue 4, 279-286, 2010.
Ratnasabapathy et al., Shoulder pain in people with a stroke: a population-based study, Clinical Rehabil, 17, 304-311, 2003.
Renzenbrink et al., Percutaneous neuromuscular electrical stimulation (P-NMES) for treating shoulder pain in chronic hemiplegia,.,. Clinical Rehabil, 18, 359-365, 2004.
Rajararn et aL, Shoulder forearm support for the subluxed shoulder, Arch Phys Med Rehabil, vol. 66, pp. 191-192, Mar. 1985.
D J Price, The shoulder block: a new alternative to interscalene brachia! plexus blockade for tM control of postoperative shoulder pain, Anaesth Inten Care, 35, 5"75-581, 2007.
Knutson et al., Electrode fracture rates and occurrences of infection and granulorna associated with precutaneous . . . J of Rehab Res Dev, vol. 39, No. 6, pp. 671-684, Nov./Dec. 2002.
Picaza et aL, Pain Suppression by Pheriphera! Nerve Stimulation Chronic Effects of Implanted Devices, Appl Neurophysiol, 40, pp. 223-234, 1977/78.
Picaza et al., Pain Suppression by Pheripheral Nerve Stimulation Part I Observations with Transcutaneous Stimuli, Surg Neurol, vol. 4, pp. 105-1 14, Jul. 1975.
Picaza et al., Pain Suppression by Pheripheral Nerve Stimulation Part II Observations with Implanted Devices, Surg Neurol, vol. 4, pp. 115-126, Jul. 1975.
North et al, Spinal cord stimulation for chronic, intractable pain: superiority of "multi-channel" devices, Pain 44, pp. 119-130, 1991.
R North, Spinal cord and peripheral nerve stimulation: technical aspects, Pain Research and Clinical Management, Elsevier, vol. 15 (Ch 12), pp. 183-195, 2003.
Nashold et al., Long-term pain control by direct peripheral-nerve stimulation, The Journal of Bone and Joint Surgery, vol. 64-A, No. 1, pp. 1-10, Jan. 1982.
Nashold et al., Electrical stimulation of peripheral nerves for relief of intractable chronic pain, Medical Instrumentation, vol. 9, No. 5, pp. 224-225, Sep./Oct. 1975.
Nashold et aL, Peripheral nerve stimulation for pain relief using a multicontact electrode system, J Neurosurg, 51, pp. 872-873, 1979.
Mortimer et aL, Intramuscular Electrical Stimulation: Tissue Damage, Annals Biomed Eng, vol. 8, pp. 235-244, 1980.
Moe et al., Functional Electrical Stimulation for Ambulation in Hemiplegia, The Journal Lancet, pp. 285-288, Jul. 1962.
Lindgren et al, Shoulder Pain After Stroke A Prospective Population-Based Study, Stroke, pp. 343-348, Feb. 2007.
Loeb et al., The BION devices: injectable interfaces with preipheral nerves and muscles, Neurosurg Focus, 20(5):E2, pp. 1-9, 2006.
Melzack et al., On the Nature of Cutaneous Sensory Mechanisms, Brain, 85, pp. 331-356, Jun. 1962.
Lynch et al, Continuous passive motion improves shoulder joint integrity following stroke, Clinical Rehabilitaiton, 19, pp. 594-599, 2005.
Long MD, Electrical stimulation for relief of pain from chronic nerve injury, J Neurosurg, vol. 39, pp. 718-722, Dec. 1973.
Loeser MD, The Future Will pain be abolished or just pain specialists?, Minnesota Medicine, pp. 20-21, Jul. 2001.

\* cited by examiner

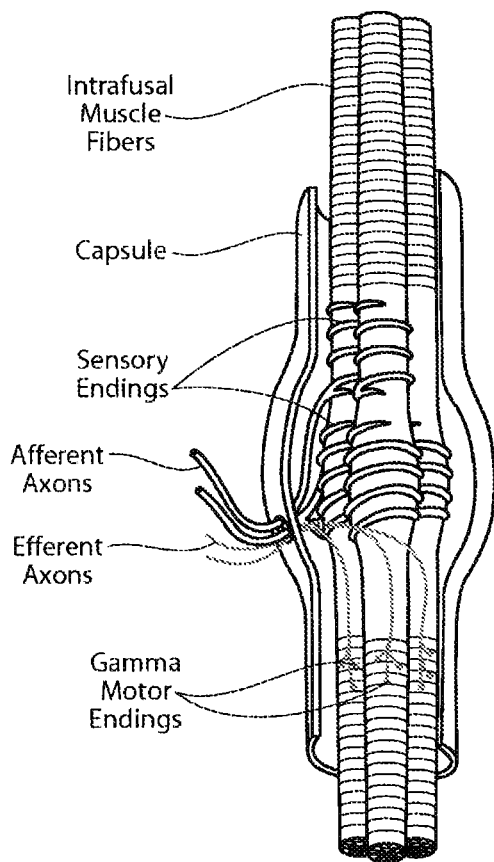
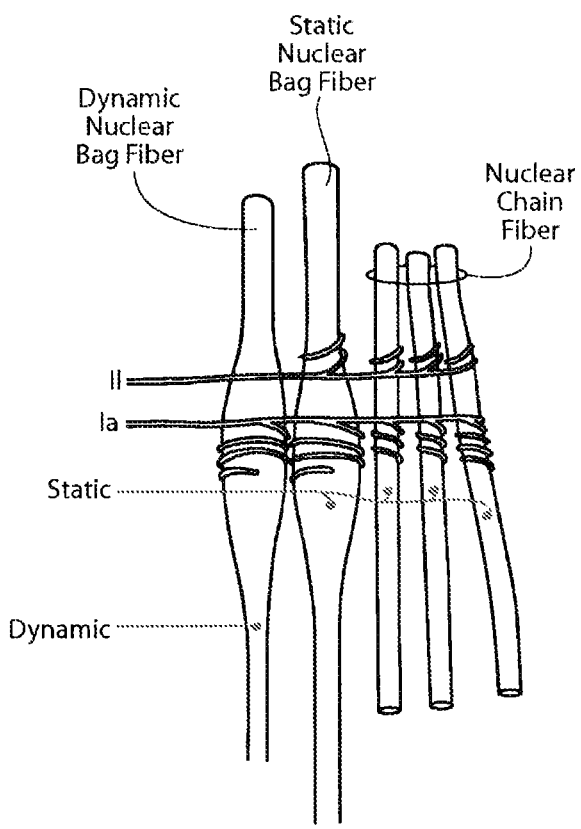
Fig. 2A
Fig. 2B

SYSTEMS AND METHODS FOR THE TREATMENT OF PAIN THROUGH NEURAL FIBER STIMULATION

CROSS-REFERENCE TO RELATED APPLICATION

This application is a continuation of U.S. patent application Ser. No. 15/854,206, entitled "Systems and method for the treatment of pain through neural fiber stimulation," filed on Dec. 26, 2017, which is a continuation of U.S. patent application Ser. No. 15/453,978, entitled "Systems and method for the treatment of pain through neural fiber stimulation," filed on Mar. 9, 2017, now U.S. Pat. No. 9,855,427, which is a continuation of U.S. patent application Ser. No. 14/336,633, entitled "Systems and methods for the treatment of pain through neural fiber stimulation" filed on Jul. 21, 2014, now U.S. Pat. No. 9,616,229, which is a continuation of U.S. patent application Ser. No. 13/309,024, entitled "Systems and methods for the treatment of pain through neural fiber stimulation" filed on Dec. 1, 2011, now U.S. Pat. No. 8,788,046, which claims the benefit of U.S. Provisional Patent Application Ser. No. 61/418,801, filed 1 Dec. 2010, and is entitled "Systems and Methods for the Treatment of Pain Through Neural Fiber Stimulation," and also claims the benefit of U.S. Provisional Patent Application Ser. No. 61/418,768, filed 1 Dec. 2010, and entitled "Systems and Methods to Place One or More Leads in Tissue to Electrically Stimulate Nerves to Treat Pain," all of which are hereby incorporated by reference. U.S. patent application Ser. No. 13/309,024 is a continuation-in-part of U.S. patent application Ser. No. 13/294,875, filed 11 Nov. 2011, and entitled "Systems and Methods to Place One or More Leads in Tissue to Electrically Stimulate Nerves to Treat Pain," which claims the benefit of U.S. Provisional Patent Application Ser. No. 61/412,685, filed 11 Nov. 2010, and entitled "Systems and Methods to Place One or More Leads in Tissue to Electrically Stimulate Nerves to Treat Pain," which are all incorporated by reference herein in their entirety.

BACKGROUND OF THE INVENTION

Embodiments according to the present invention relate generally to the relief of bodily pain in an animal, such as a human, and more specifically to the treatment of pain by action potential activation in neural fibers.

The peripheral nervous system of an animal, such as a human, is comprised generally of efferent (motor) and afferent (sensory) neural fibers. Efferent fibers generally carry motor action potentials from the central nervous system, while afferent fibers carry sensory action potentials to the central nervous system. Since the 1950's and 1960's and the codification of the gate theory, it has been generally accepted that bodily pain results from activity in nociceptive and non-nociceptive, or somatosensory, afferent nerve fibers, and the interaction of neural signals and pathways, which are influenced by several psychological and physiologic parameters. For instance, in a healthy person, action potentials transmitted along non-nociceptive fibers do not normally generate or cause a perception of pain. However, in persons experiencing chronic pain (e.g., when a person becomes overly sensitized to pain), non-noxious stimuli, and hence the activity of non-nociceptive fibers, can cause pain. This means that in a chronic pain state, sensations that would not be perceived as pain in a healthy person (e.g. light pressure or touch) may actually be perceived as painful. That is, in an individual that experiences chronic pain, the non-noxious stimuli that are sensed (transduced) by non-nociceptive receptors can lead to a perception of pain. Generally, however, while nociceptive afferent activity "opens" a gate to the transmission of sensory action potentials related to noxious input, non-nociceptive afferent activity "closes" the gate, thereby preventing or inhibiting the transmission of such sensory signals to the brain, interrupting or reducing the perception of pain.

Prior methods of stimulation of nerves for the reduction of pain, described below, have focused on the stimulation of afferent neural fibers, and such focus is perhaps understandable due to the conventional wisdom in the art for the past five decades related to gate control theory. However, prior nerve stimulation modalities used to treat pain, especially with regards to peripheral nerves, recognized a narrow treatment window between stimulation settings that may achieve desired analgesia through sensory stimulation of non-nociceptive afferents and stimulation settings that reach the threshold for discomfort or motor stimulation of efferent fibers, the latter thought to be undesirable for a number of reasons. Supplementary to such conventional wisdom, and as described in further detail below, recruitment of efferent fibers is thought to be actually beneficial in reducing pain.

The electrical stimulation of nerves, often afferent nerves, to indirectly affect the stability or performance of a physiological system can provide functional and/or therapeutic outcomes, and has been used for activating target nerves to provide therapeutic relief of pain. While prior systems and methods can provide remarkable benefits to individuals requiring therapeutic pain relief, many issues and the need for improvements still remain.

Electrical stimulation systems have been used for the relief of pain. Despite the recognition and use of electrical stimulation for the treatment of pain, widespread use of available systems is limited. Such limited use is thought to stem from a variety of factors, such as invasiveness of required surgical procedures (e.g. lead placement in epidural space of spinal cord or surgical dissection), risk of surgical complications associated with such procedures (e.g. infection, hemorrhage, neurologic injury, and/or spinal fluid leaks), the technical skill and training required to place the electrode(s), the duration of time required to place the electrode(s) correctly, the supporting equipment (e.g. imaging equipment such as fluoroscopy) required for electrode placement, risk of device complications (e.g. migration of stimulating lead or catastrophic failure, or breakage, of such lead), and/or loss of pain relief over time.

Electrical stimulation systems may be provided as either external or implantable devices, or a combination thereof, for providing electrical stimulation to activate nerves to provide therapeutic relief of pain. These "neurostimulators" are able to provide treatment and/or therapy to individual portions of the body. The operation of these devices typically includes the use of (i) an electrode placed either on the external surface of the skin, and/or (ii) a surgically implanted electrode. In most cases, one or more surface electrodes, cuff-style electrodes, paddle-style electrodes, spinal column electrodes, percutaneous leads, and/or leadless microstimulators incorporating integral electrodes, each having one or more electrodes, may be used to deliver electrical stimulation to one or more select portions of a patient's body.

One example of an electrical stimulation system used to treat pain is a transcutaneous electrical nerve stimulation (TENS) system, which has been cleared by the U.S. Food and Drug Administration (FDA) for treatment of pain. TENS systems are external neurostimulation devices that employ electrodes placed on an external skin surface to activate target afferent nerve fibers below the skin surface. Advantageously, TENS has a low rate of serious complications, but disadvantageously, it also has a relatively low (i.e., approximately 25% or less) long-term rate of success, and some of its success is attributed to a placebo effect. Additionally, TENS has low long-term patient compliance because it may cause additional discomfort by generating cutaneous pain signals due to the electrical stimulation being applied through the skin, the electrodes may be difficult to apply, and the overall system is bulky, cumbersome, and not suited for long-term use.

In addition, several clinical and technical issues associated with surface electrical stimulation have prevented it from becoming a widely accepted treatment method. First, stimulation of cutaneous pain receptors often cannot be avoided resulting in stimulation-induced pain that limits patient tolerance and compliance. Second, electrical stimulation may be delivered at a relatively high frequency to prevent stimulation-induced pain, which leads to early onset of muscle fatigue in turn preventing patients from properly using their muscle(s). Third, it is difficult to stimulate deep nerves and/or muscles with surface electrodes without stimulating overlying, more superficial nerves and/or muscles resulting in unwanted stimulation. Finally, clinical skill and intensive patient training is required to place surface electrodes reliably on a daily basis and adjust stimulation parameters to provide optimal treatment. The required daily maintenance and adjustment of a surface electrical stimulation system is a major burden on both patient and caregiver.

Other electrical stimulation systems that have been employed to treat pain include spinal cord stimulation (SCS) systems, which are also FDA approved as implantable neurostimulation devices marketed in the United States for treatment of pain. Similar to TENS, when SCS evokes paresthesias that cover a region of pain, it confirms that the location of the electrode and the stimulus intensity should be sufficient to provide pain relief and pain relief can be excellent initially, but maintaining sufficient paresthesia coverage is often a problem due to lead migration along the spinal canal.

Spinal cord stimulation is limited by the invasive procedure and the decrease in efficacy as the lead migrates. When it can produce paresthesias in the region of pain, spinal cord stimulation is typically successful initially in reducing pain, but over time the paresthesia coverage and pain reduction is often lost as the lead migrates away from its target.

Lead migration is the most common complication for SCS systems, occurring in up to 40% or more of the cases. When the lead migrates, the active contact moves farther from the target fibers and loses the ability to generate paresthesias in the target area. SCS systems attempt to address this problem by using leads with multiple contacts so that as the lead moves, the next contact in line can be selected to be the active contact. Additionally, multiple contacts can be used to guide or steer the current toward the targeted nerve fibers and away from the non-targeted nerve fibers. Although this approach may be successful, it often requires time-intensive and complex programming, adding to the overall cost of the therapy and the burden on the patient and caregiver(s).

Peripheral nerve stimulation has been attempted and may be effective in reducing pain, but it previously required specialized surgeons to place cuff- or paddle-style leads on or around the nerves in a time-consuming and invasive surgical procedure. Such prior procedures may include the use of ultrasound-guided lead placement in an attempt to avoid placement in muscle tissue in an attempt to coapt intimately an electrode surface with a target nerve, or approximately 3 millimeters or less from the nerve.

Accordingly, the art of pain reduction by neural activation would benefit from systems and methods that improve pain reduction.

SUMMARY OF THE INVENTION

Embodiments of the present invention include improved systems and methods of pain reduction by inducing action potentials in target neural structures. Action potentials may be generated or activated in efferent fibers as an alternative to or in addition to activation of afferent fibers. If an action potential is directly induced in select afferent fibers, such action potentials may be patterned so as to be biomimetic or stochastic, as explained below. Stimulation may be applied to targeted neural fibers located (1) neurologically upstream from a perceived point of pain (i.e. neurologically between the perceived point of pain and the central nervous system) such as to target neural fibers of nerves of passage, (2) at or near a neurological motor point, and/or (3) neurologically downstream from such motor point, where such downstream stimulation may be applied to or near a target region from which a patient is perceiving pain.

A method according to the present invention includes the step of stimulating efferent nerve fibers to generate an action potential in the efferent nerve fibers in an animal, such as a human, to reduce a perception of pain by the animal. In one embodiment, the stimulating step includes electrical stimulation.

According to one aspect of a method according to the present invention, the efferent nerve fibers are located outside a neurological motor point and outside a central nervous system of the human. The efferent nerve fibers may be located between a neurological motor point and the central nervous system of the human.

According to another aspect of a method according to the present invention, the efferent nerve fibers include motor axons, such as A$\alpha$ axons that may activate extrafusal muscle fibers and/or A$\gamma$ axons that may activate intrafusal muscle fibers.

According to still another aspect of a method according to the present invention, the method may further include the step of activating afferent nerve fibers, such as those that are in neural communication with neural receptors, such as proprioceptors. The activation of the afferent nerve fibers may result from a transduction of a physiological response to the step of electrically stimulating efferent nerve fibers. Such physiological response may be a contraction of extrafusal muscle fibers or intrafusal muscle fibers.

Another method according to the present invention is a method of reducing a perception of pain by an animal, such as a human, of a hypersensitized portion of the animal nervous system. Such method includes the step of applying electrical stimulation to at least a portion of the nervous system to cause a reduction of perception of pain by the animal.

According to still another aspect of a method according to the present invention, the applying step ay be performed for a predetermined treatment time, and the reduction of perception of pain may occur at least partially during the treatment time and at least a portion of the reduction of perception of pain may be maintained after the end of the predetermined treatment time.

According to yet another aspect of a method according to the present invention, the animal is a human and the portion of the nervous system comprises efferent nerve fibers located neurologically between and outside a neurological motor point and a central nervous system of the human.

BRIEF DESCRIPTION OF THE DRAWINGS

FIG. 2A depicts an example of a muscle spindle (shown contained in the capsule), including the intrafusal muscle fibers (innervated by type γ (gamma) (Class Aγ) motor neurons (efferent axons) and by sensory neurons (afferent axons)). The efferent (gamma) axons terminate (shown by Gamma Motor Endings) on and innervate the spindle's intrafusal muscle fibers. The sensory endings of the primary (group Ia) afferent axons and a secondary (group II) afferent axons innervate the intrafusal fibers.

FIG. 2B depicts intrafusal motor fibers (nuclear chain fibers and nuclear bag fibers) and their sensory innervation. The group II afferent axons are shown innervating the nuclear chain fibers and the static nuclear bag fiber. The group Ia afferent axons are shown wrapping around and innervating the nuclear chain fibers, the static nuclear bag fiber, and the dynamic nuclear bag fiber. The figure also indicates which portions can be considered contractile and non-contractile.

DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention, which is defined by the claims.

As described in the Background section, above, the nervous system of an animal generally comprises efferent and afferent neural fibers, and prior pain reduction modalities have focused on action potential generation or activation in non-nociceptive afferent neural fibers to inhibit, or "close the gate" to, the transmission of nociceptive pain signals to the brain. This has come to be known as the gate control theory of pain management. Most afferent fibers, however, are not bundled only with other afferent fibers; rather, the majority of nerves found amenable to peripheral nerve stimulation are nerve bundles comprising both afferent and efferent fibers.

Figure 1:
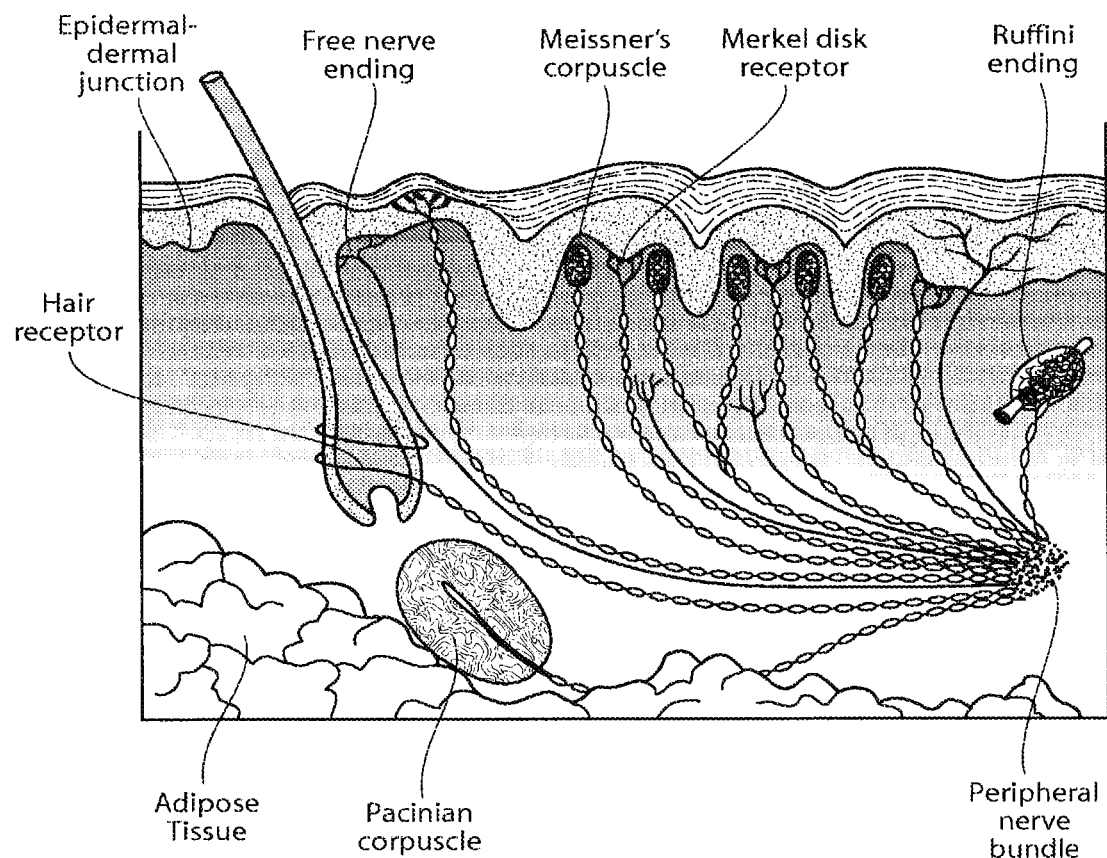
FIG. 1 depicts various physiological structures for reference in connection with the following disclosure.
Figure 2C:
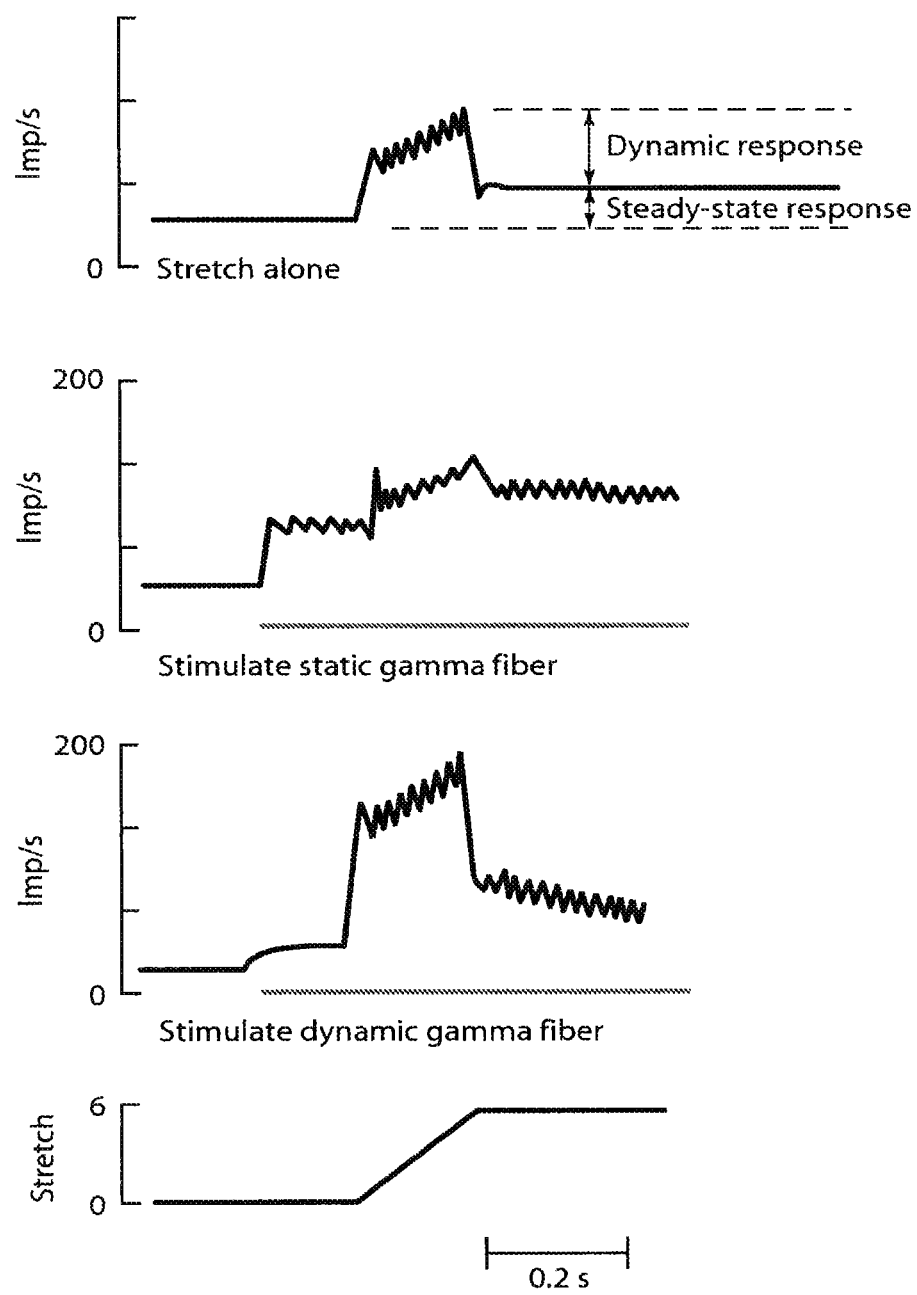
FIG. 2C depicts an example of how stretch alone or in combination with stimulation of a static gamma fiber or a dynamic gamma fiber can change the neural activity of the respective afferents axons innervating the fibers of the muscle spindle. Activation of gamma motor neurons (efferent axons), which activate the intrafusal muscle fibers, can change the frequency (Imp/s) of neural activity and stretch-sensitivity of the afferent neurons. The figure also depicts an example of the possible relative steady-state and dynamic responses that may be achieved in terms of the neural activity of an afferent neuron innervating a muscle spindle fiber.
Figure 3:
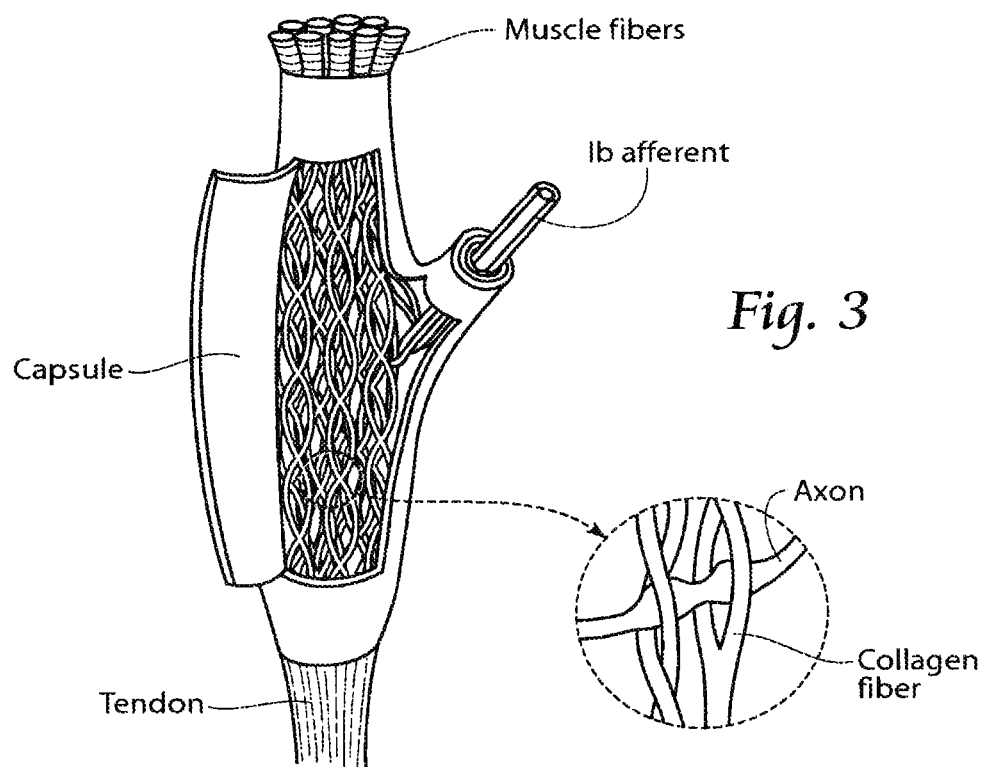
FIG. 3 depicts a Golgi tendon organ including collagen fibers that physically interact with afferent axons to generate an action potential thereon during stretch.

With reference also to FIGS. 1-3, electrical stimulation provided according to systems and methods of the present invention may mediate pain relief by activating somatosensory pathways that may be associated with mechanoreceptors, thermoreceptors, proprioceptors, and/or chemoreceptors. Generally, types of neural cells, axons, nerve fibers, or physiological structures that may be affected, such as by intra- or extra-muscle (e.g., in subcutaneous, connective, adipose, or other tissue) electrical stimulation, include functional afferent types A and C axons and efferent type A axons.

The afferent axons may be classified as Aα (type Ia or Ib), Aβ (type II), Aδ (type III), or C (type IV). Aα (type Ia) fibers are generally recognized as being associated with the primary sensory receptors of the muscle spindle, such as for transducing muscle length and speed. These fibers are myelinated, usually having a diameter from about 9 to about 22 micrometers (μm), although other diameters have been observed and may be included, and a conduction velocity of about 50 to about 120 meters per second (m/s), which is known to be proportional to the diameter of the fiber for both this type and other types of myelinated fibers. Aα (type Ib) fibers are generally recognized as being associated with Golgi tendon organs, such as for transducing muscle contraction. These fibers are myelinated, having a diameter from about 9 to about 22 micrometers (μm) and a conduction velocity of about 50 to about 120 meters per second (m/s). Aβ (type II) fibers are generally recognized as being associated with the secondary sensory receptors of the muscle spindle, such as for transducing muscle stretch. These fibers are also associated with joint capsule mechanoreceptors (as transduces joint angle) and all cutaneous mechanoreceptors. The cutaneous mechanoreceptors may include Meissner's corpuscles, Merkel's discs, Pacinian corpuscles, Ruffini corpuscles, hair-tylotrich (for sensing stroking/fluttering on the skin or hair), and the field receptor (for sensing skin stretch).

Meissner's corpuscles are nerve endings that can be found in the skin, which transmit afferent information regarding touch (such as soft, or light, touch) and/or vibration, especially at vibration frequencies of less than 50 Hertz. These fibers are rapidly adaptive receptors that are often located below the epidermis within the dermal papillae. The corpuscles may be found as encapsulated unmyelinated nerve endings, comprising flattened supportive cells arranged as horizontal lamellae surrounded by a connective tissue capsule. Examples of this corpuscle have been described as having a length of about 30 to about 140 μm and a diameter of about 40 to about 60 μm.

Merkel's discs are a type of mechanoreceptor found in the skin, hair follicles, and in the oral and anal mucosa. The discs transmit afferent information regarding pressure and texture. Sometimes referred to as a Merkel disc receptor or Merkel cell-neurite complex, the nerve ending comprises a Merkel cell next to a nerve terminal. A single afferent nerve fiber may innervate multiple nerve endings, such as 50-100 endings. This mechanoreceptor is an unencapsulated, slowly adapting type I mechanoreceptor that will provide a non- or minimally-decaying response to pressure. The Merkel disc receptor may have two phases of firing, dynamic and static. In the static phase, an irregular activity may be observed, which may be typical of slowly adapting type I mechanoreceptors but contrasts with the regular pattern of slowly adapting type II mechanoreceptors.

Pacinian corpuscles are nerve endings that may be found in the skin. They may also be found in the mesentery, between layers of muscle, and on interosseous membranes between bones. Pacinian corpuscles transmit afferent information regarding pain and pressure. For instance, these corpuscles may detect gross pressure changes and vibrations and may fire in response to quick changes in joint position. They are phasic tactile mechanoreceptors that can detect deep pressure because they are found below the skin surface, usually in the dermis, and comprise some free nerve endings.

Ruffini corpuscles are slowly adapting mechanoreceptors that may be present in the glabrous dermis (hairless skin) and subcutaneous tissue of humans. These corpuscles transmit afferent information regarding skin stretch, movement, position (such as position of the fingers), and sense of control (such as slipping of objects along the skin surface). This type of receptor may have a spindle shape, and they may be found in the deep layers of the skin, allowing them to indicate continuous pressure states and mechanical joint deformation, such as joint angle change.

The Aβ fibers are myelinated, usually having a diameter from about 6 to about 12 micrometers (μm), although other diameters have been observed and may be included, and a conduction velocity of about 33 to about 75 meters per second (m/s).

Aδ (type III) fibers are generally recognized as being associated with free nerve endings of touch and pressure (for sensing excess stretch or force), hair-down receptors (for sensing soft, or light, stroking), nociceptors of the neospinothalamic tract, and cold thermoreceptors. These fibers are thinly myelinated, having a diameter from about 1 to about 5 micrometers (μm) and a conduction velocity of about 3 to about 30 meters per second (m/s).

C (type IV) fibers are generally recognized as being associated with nociceptors of the paleospinothalamic tract, and warmth thermoreceptors. These fibers are unmyelinated, having a diameter from about 0.2 to about 1.5 micrometers (μm) and a conduction velocity of about 0.5 to about 2.0 meters per second (m/s).

As mentioned above, most nerve bundles include both afferent and efferent fibers. The efferent axons may be classified as Aα or Aγ. Aα efferent fibers are generally recognized as being associated with extrafusal muscle fibers. These fibers are myelinated, having a diameter from about 13 to about 20 micrometers (μm) and a conduction velocity of about 50 to about 120 meters per second (m/s). Aγ efferent fibers are generally recognized as being associated with intrafusal muscle fibers. These fibers are myelinated, having a diameter from about 5 to about 8 micrometers (μm) and a conduction velocity of about 20 to about 40 meters per second (m/s).

A first method according to the present invention includes activating afferent fibers (e.g. type Ia, Ib, and/or II, which may also be called Aα and/or Aβ afferent fibers), which are physically located in an area from or in which an animal is perceiving pain. When a fiber is referred to herein as "activated," it is to be understood that at least one action potential is generated or initiated by or along, or propagated along, such fiber in response to some form of stimulation. Such afferent fiber activation may mediate pain relief by activation of afferent pathways associated with primary receptors of muscle spindles, Golgi tendon organs, secondary receptors of muscle spindles, joint receptors, touch receptors (e.g. Meissner's corpuscles, Merkel disk receptors, Pacinian corpuscles, Ruffini endings, etc.) other types of mechanoreceptors (e.g. joint capsule mechanoreceptors), and/or proprioceptors. As a non-limiting example, stimulation may activate one or more Aβ fibers that carry afferent information from a mechanoreceptor (i.e. a sensory receptor) that responds to mechanical pressure or distortion. The stimulation may be applied in muscle or in non-muscle tissue (e.g. subcutaneous, connective, adipose or other tissue). Non-limiting examples of mechanoreptor pathways that may be activated by stimulation include (1) one or more Pacinian corpuscles; (2) one or more Meissner's corpuscles; (3) one or more Merkel disc receptors; and/or (4) one or more Ruffini corpuscles. The applied stimulation may mediate pain relief through the activation of nerve fibers associated with, and/or innervating, receptors that are rapidly adapting, intermediate adapting, and/or slowly adapting. While stimulation may be applied directly to target nerves, an electrode, as more fully described below, is preferably spaced a predetermined distance, or within a predetermined range of distances, from the target nerve fibers.

A second method according to the present invention comprises the step of activating one or more afferent nerve fibers that may be located outside an area from or in which an animal is perceiving pain, and may or may not be associated with the mentioned receptors. Such stimulation may be beneficial to patients experiencing pain in regions no longer innervated or that were not previously innervated by the target fibers, such as those patients that may have had removal of, or damage to, their afferent receptors. Examples of such situation may be amputee phantom limb pain or tissue damage due to trauma, such as burns, or surgery. Other indications in which such stimulation may provide beneficial perceived reduction in pain are pathological or disease states (e.g. induced by chemotherapy, vascular insufficiency, cancer, or diabetes) or other considerations that may prevent activation of receptors by physiological transduction. Other considerations my include areas of the body that are sensory-only areas, such as the sural nerve, or areas in which the receptors may be intact, but it may be preferable not to activate them. For instance, if a nerve trunk (e.g. femoral or sciatic nerve) is being stimulated, large contractions may be undesirable due to the physical effect of same. Additionally or alternatively, tissue damage or disease progression dictate or influence the placement of needles and/or electrodes; for instance, if a patient suffers from complex regional pain syndrome, it may be desirable to prevent insertion of a needle in the affected area, as it may make symptoms of the syndrome worse, but a needle may be inserted outside of the affected area with less risk.

Figure 4A:
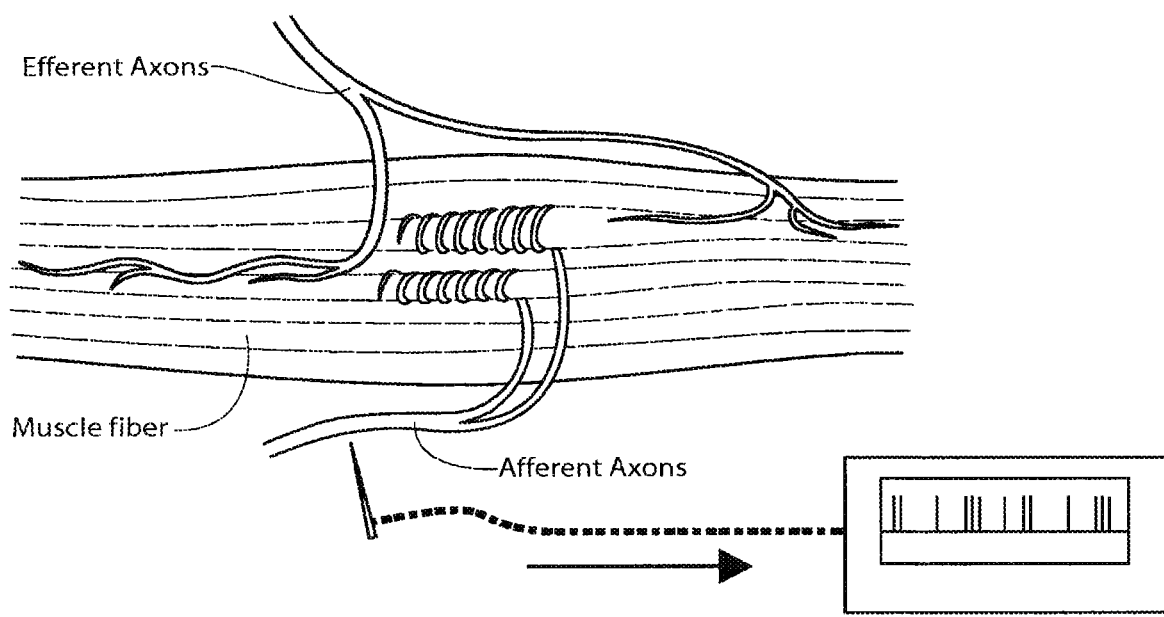
FIG. 4A provides a diagrammatic view of electrode placement near a targeted sensory neural structure according to a sensing step of a second embodiment of a method according to the present invention.
Figure 4B:
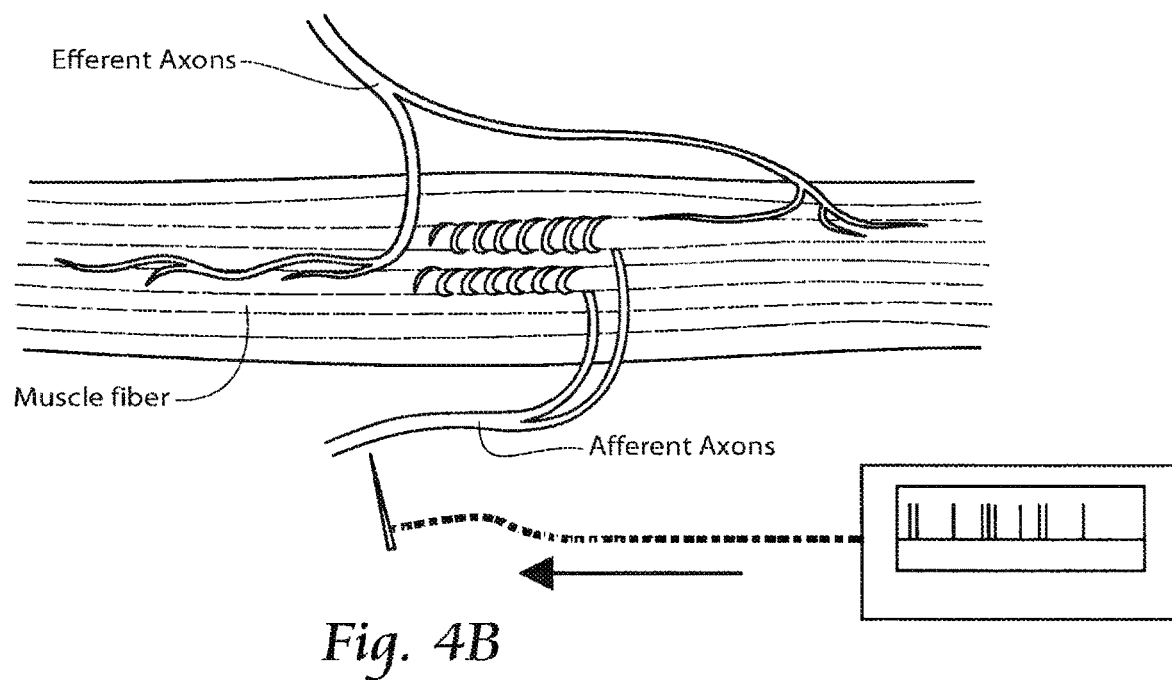
FIG. 4B provides a diagrammatic view of electrode placement near a targeted sensory neural structure according to a stimulating step to occur after or without the sensing step of FIG. 4A.
Figure 5:
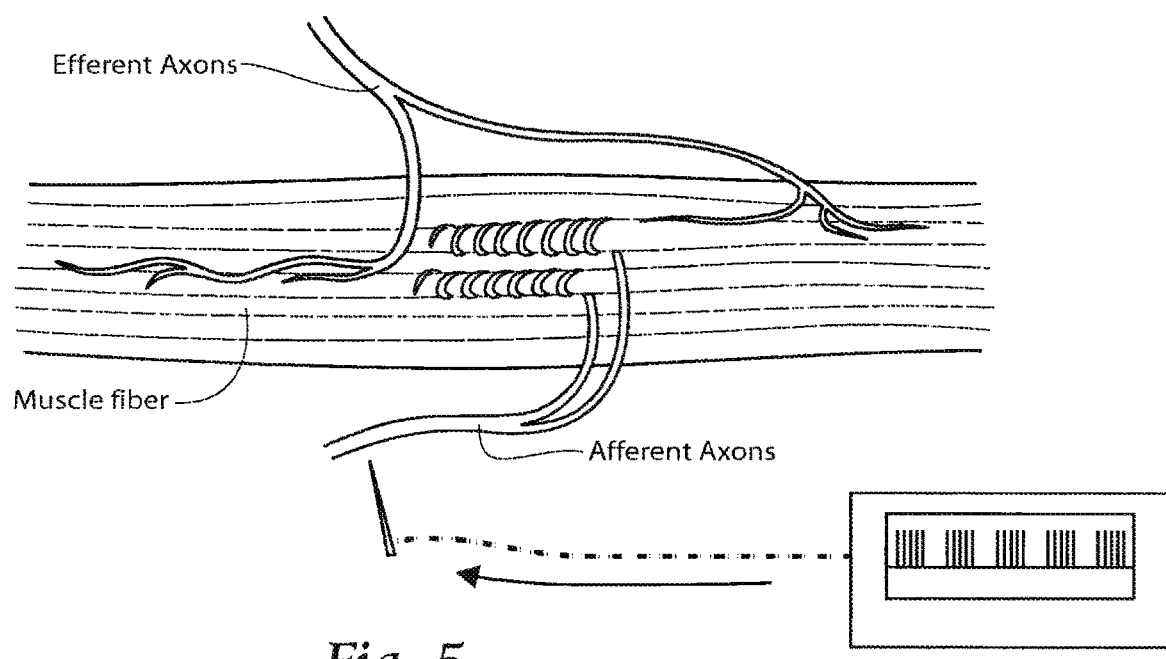
FIG. 5 provides a diagrammatic view of electrode placement near a targeted sensory neural structure according to a first embodiment of a method according to the present invention.

In any method according to the present invention involving direct stimulation of afferent nerve fibers and/or afferent receptors, with or without efferent fiber recruitment, the stimulation is preferably provided in one or both of two ways: (1) direct mimicked (or biomimetic) afferent stimulation and/or (2) modulated high frequency-induced stochastic response. With respect to direct mimicked afferent stimulation, stimulation is applied in a predetermined, random, or pseudo-random manner to mimic afferent neural activity that otherwise may naturally occur in response to activity normally sensed by the target afferents. For example, afferents, including type Ia fibers associated with the muscle spindle (as shown in FIGS. 2A-B) and type Ib fibers associated with Golgi tendon organs (as shown in FIG. 3), and possibly others, normally respond, and fire multiple, temporally patterned action potentials in response to a muscle contraction. To predetermine a stimulation pattern, afferent neural activity—in response to applied efferent stimulation or cued, or prompted, voluntarily generated muscle activity, such as contraction or stretch—may be recorded and/or analyzed, as diagrammatically depicted in FIG. 4A. The recorded or analyzed pattern may be obtained directly from the animal to be relieved of pain, may be obtained directly from an animal that is not the animal to be relieved of pain (live model), may be calculated or modeled from one or more patterns obtained from one or more animals (including or excluding the animal to be relieved of pain), and/or may be mathematically or otherwise artificially generated (i.e., without sampling). The predetermined pattern of afferent stimulation to be applied according to the present invention may then be established to approximate or identically mimic at least a portion of the recorded or analyzed pattern, as diagrammatically shown in FIG. 4B. Additionally or alternatively, a random or pseudo-random stimulation pattern may be applied to the afferent fibers to mimic natural afferent activity. The stimulation patterns applied may include variations in duty cycle and/or in stimulation waveform shape and/or pulse parameters, such as frequency, pulse width, and/or amplitude, which may be varied between applied pulses, or during a pulse, which may have the effect of modifying waveform shapes. Altered stimulation patterns may additionally or alternatively utilize a pre-pulse, which may be the same or opposite polarity as a treatment pulse, and may have the same or opposite polarity thereof. With respect to the second way, specified as modulated, high-frequency-induced stochastic response and as diagrammatically depicted in FIG. 5, naturally occurring afferent action potentials (occurring in response to stimuli) may be generated or approximated as a result of an applied electrical stimulation at a modulated high frequency. For example, a relatively high frequency from about 1 kHz to about 20 kHz, preferably about 4 kHz, modulated at a reduced frequency, such as about 0.1 Hz to about 1 kHz, more preferably less than 50 Hz, such as 1-30 Hz, and more preferably at about 12-16 Hz, may be used. Such stimulation may generate pseudo-random patterns of activity in the affected afferent nerve fibers.

Example of Direct Afferent Action Potential Stimulation

The treatment of pain through direct afferent fiber stimulation may demonstrate dis-sensitization of the afferent neural tissues that naturally respond to such stimulation. That is, it is generally recognized that the perception of pain, especially non-acute pain such as sub-acute or chronic pain, in mammals can be caused, worsened, and/or sustained in duration by a sensitization of afferent sensory receptors and/or the central nervous system fibers that receive direct and/or indirect signals from the afferent sensory receptors, including free nerve endings, to noxious or conventional or previously non-noxious stimuli. Sensitization is the process whereby previously non-noxious stimuli are perceived as painful, and this is an integral part of the development and maintenance of chronic pain (as opposed to the acute, healthy pain response). Such sensitization may result from non-nociceptive primary afferents (e.g. $A\beta$) sprouting to make inappropriate and/or additional connections in the spinal cord, from the loss of inhibition in the central nervous system (e.g. spinal cord, and/or brain), and from plasticity resulting from changes in functional connectivity. However, what has been demonstrated by certain afferent fiber stimulation for the treatment of pain is that such stimulation may actually permanently, or at least long-term, reverse the sensitization process that formed the basis for the chronic pain being treated. Accordingly, the effects of the afferent stimulation for the treatment of pain chronologically outlast the treatment duration, and such effects may exponentially outlast the treatment duration. For example, it is common for patients that have a reduced level of pain measured, observed or reported at the end of one month after a treatment cycle, such as a three-week treatment cycle, to demonstrate the same level of pain reduction up to one year or longer after the treatment cycle has concluded. Thus, dis-sensitization may be demonstrated and the pain reduction experienced at approximately the stimulation treatment duration after the end of the treatment cycle is maintained for more than 17 times the treatment duration. For example, if a patient reported a pain level of 6 prior to treatment, and a pain level of 2 at a time that is about one month after a treatment cycle (such as a three-week treatment cycle), there has been demonstrated a high probability that the patient will report a pain level of 2 at a time that is about one year after the completion of the treatment cycle. In any event, at one year after treatment, if the pain level reported by the patient is less than the pain level reported prior to treatment, then at least some dis-sensitization is thought to have occurred. Systems and methods according to the present invention may be used to treat pain felt in a given region of the body by stimulating neural fibers associated with, disposed on, or innervating muscle, subcutaneous, connective, adipose, or other tissue that may be close to or some distance away from a "nerve of passage" in a region that is superior (i.e., cranial or upstream toward the spinal column) to the region where pain is felt. Neural impulses comprising pain felt in a given muscle, organ, or cutaneous region of the body pass through spinal nerves that arise from one or more nerve plexuses. The spinal nerves in a nerve plexus, which comprise trunks that divide by divisions and/or cords into branches, comprise "nerves of passage." It has been discovered that applying stimulation in a muscle near a targeted nerve of passage relieves pain that manifests itself in a region that is inferior (i.e., caudal or downstream from the spinal column) from where stimulation is actually applied. An example of nerves of passage stimulation may be found in U.S. patent application Ser. No. 12/653,023, filed on Dec. 7, 2009, and entitled "Systems and Methods to Place One or More Leads in Tissue to Electrically Stimulate Nerves of Passage to Treat Pain," published as US2010/0152808, which is incorporated by reference herein in its entirety Alternatively or additionally, to relieve pain in a target muscle, the percutaneous or implanted lead and/or electrode may be placed in the muscle (e.g. deltoid) that is experiencing the pain near, or within a therapeutically effective distance from, the point where a motor nerve enters the muscle (i.e., the motor point).

Phantom pain (a type pain that may be experienced, e.g., post-amputation) is one example of the effectiveness of "nerves of passage" stimulation, because the bodily area in which phantom pain is perceived to originate does not physically exist. A lead and/or electrode cannot be physically placed in the muscles that hurt, because those muscles were amputated. Still, by applying stimulation in a muscle, subcutaneous, connective, adipose, or other tissue that has not been amputated at a therapeutically effective distance from a targeted nerve of passage that, before amputation, preferably natively innervated the amputated muscles, phantom pain can be treated. An example of the treatment of post-amputation pain may be found in U.S. patent application Ser. No. 12/653,029, filed Dec. 7, 2009, and entitled "Systems and Methods To Place One or More Leads in Tissue for Providing Functional and/or Therapeutic Stimulation," published as US2010/0152809, which is incorporated by reference herein in its entirety.

Chronic, sub-acute, or acute pain in existing, non-amputated muscle, subcutaneous, connective, adipose, or other tissue can also be treated by "nerves of passage" stimulation. By applying stimulation to or near a targeted nerve of passage that innervates the region where chronic, sub-acute, or acute pain is manifested, the pain can be treated.

In "nerves of passage" stimulation, a lead and/or electrode can be placed in muscle, subcutaneous, connective, adipose, or other tissue that is conveniently located near a nerve trunk that passes by the electrode and/or lead on the way to the painful area. In "nerves of passage" stimulation, the lead and/or electrode may be placed in a muscle, subcutaneous, connective, adipose, or other tissue that is not necessarily the target (painful) tissue, but rather in a muscle or other tissue that is upstream from the painful region, because the proximal muscle or other tissue presents a convenient and useful location to place the lead and/or electrode. Additionally or alternatively, the lead and/or electrode may be placed in a muscle, subcutaneous, connective, adipose, or other tissue having more than one region, to stimulate a nerve to treat the perception of pain from a different region of the same muscle or tissue. For instance, with respect to a Sartorius muscle, an electrode may be placed generally near the top of the leg (near femoral nerve (1-2 cm below femoral crease)) in a first region of the Sartorius muscle, to relieve pain felt in the inner thigh near the knee (downstream), in a second region of the Sartorius muscle.

The systems and methods make possible the treatment of chronic or acute pain in which muscle contraction cannot or should not be evoked (e.g. in the case of amputation pain in which the target area has been amputated is no longer physically present) or is otherwise undesirable, or other cases of nerve damage either due to a degenerative diseases or condition such as diabetes of impaired vascular function (in which the nerves are degenerating, and may be progressing from the periphery), or due to trauma. The systems and methods make possible the placement of one or more stimulation leads and/or electrodes in regions distant from the motor point or region of pain, e.g., where easier access or more reliable access or a clinician-preferred access be accomplished; or in situations where the motor nerve point is not available, damaged, traumatized, or otherwise not desirable; or in situations where it is desirable to stimulate more than one motor point with a single lead and/or electrode; or for cosmetic reasons; or to shorten the distance between the lead and its connection with a pulse generator; or to avoid tunneling over a large area or over or across a joint, where the latter may contribute to device failure.

Figure 6A:
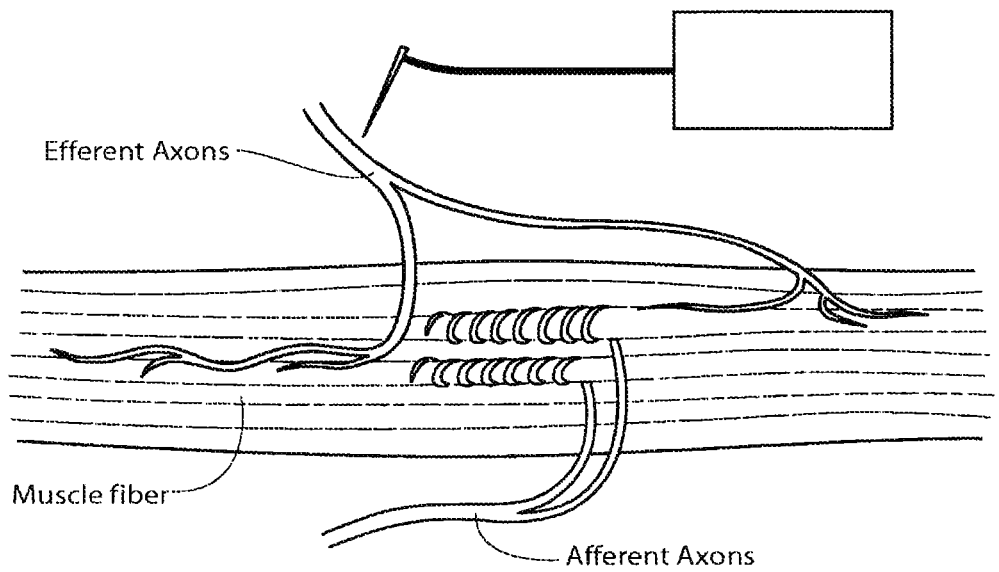
FIG. 6A provides a diagrammatic view of electrode placement near a targeted neural structure according to a third embodiment of a method according to the present invention.
Figure 6B:
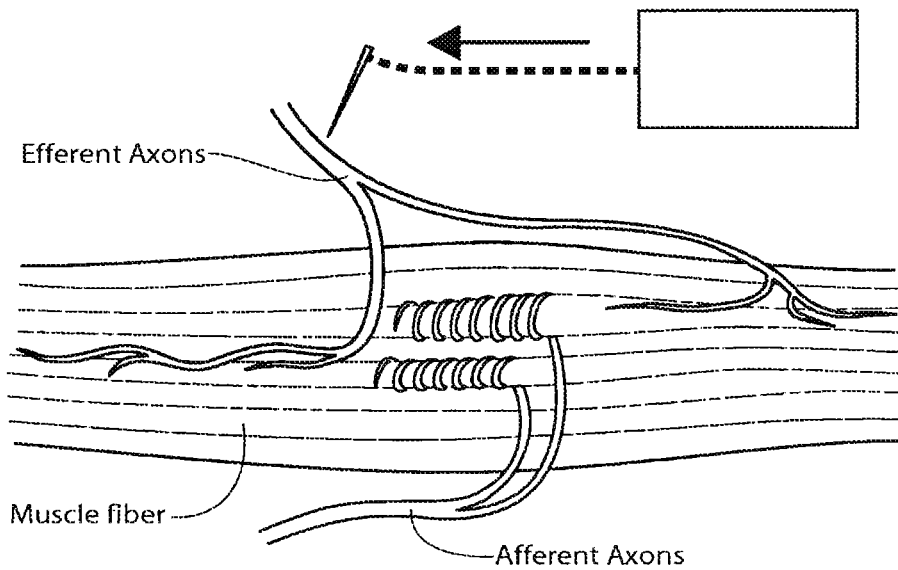
FIG. 6B provides a diagrammatic view of a muscle contraction caused by electrical stimulation by the electrode of FIG. 6A.
Figure 7A:
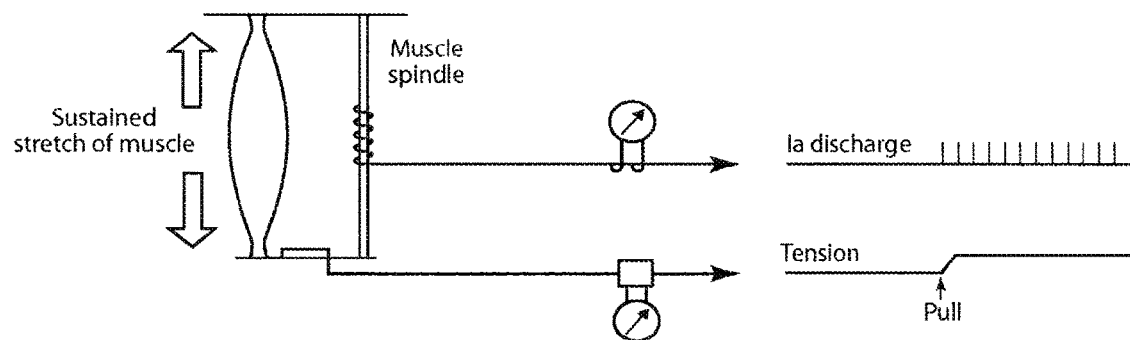
FIG. 7A provides a diagrammatic view of afferent neural structure activation or firing in response to a muscle stretch.
Figure 7B:
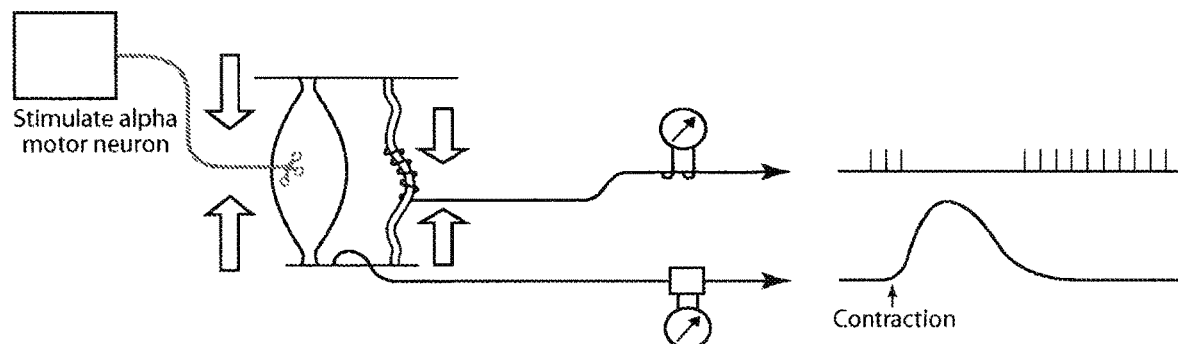
FIG. 7B provides a diagrammatic view of stretch receptor afferent neural structure activation, as perhaps by a weighted stretch, and stretch receptor afferent neural fiber deactivation during muscle contraction caused by electrical stimulation of efferent neural structures.
Figure 7C:
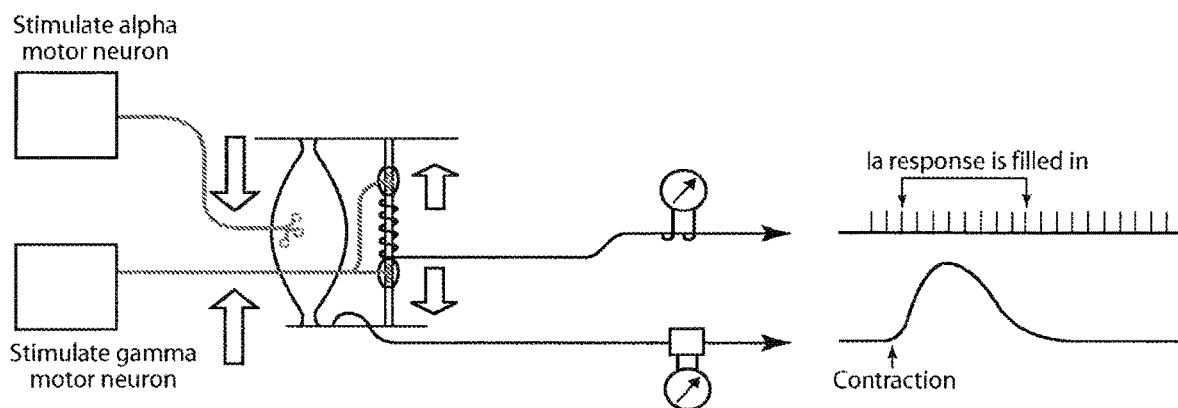
FIG. 7C provides a diagrammatic view of a method of continuing afferent activation during the contraction of FIG. 7B through stimulation of additional or alternative efferent neural structures to those efferent structures stimulated in FIG. 7B.

A third method according to the present invention, as diagrammatically depicted in FIGS. 6A-B, comprises the step of activating one or more motor (efferent) axons (type $A\alpha$ or $A\beta$) which can, in turn, mediate pain relief by activating extrafusal muscle fibers and/or intrafusal muscle fibers. Activation of extrafusal muscle fibers (e.g. via activation of motor ($A\alpha$) axons) can generate and/or modulate responsive afferent activity by contracting muscle fibers, producing tension, and/or causing skeletal movement. The action (e.g. contraction, tension, movement, etc.) produced by efferent activity may be transduced by sensory endings or fibers and transmitted via afferent fibers to the central nervous system, which can mediate pain relief. Activation of intrafusal muscle fibers (e.g. via activation of motor ($A\gamma$) axons) can modulate and/or generate afferent activity by changing afferent firing rate or pattern (e.g. the relative base or steady-state firing frequency, average thereof, and/or the transient firing frequency such that the running average may or may not vary over time according to a pattern or non-patterned sequence) and/or the afferent's sensitivity to mechanical or other stimuli such as stretch, vibration, muscle contraction, etc. One method of providing pain relief is to activate neurons (or neural structures) innervating (or considered part of) proprioceptors, modifying proprioception. In either case, of activation of intrafusal (via $A\gamma$ efferent axons) and/or extrafusal (via $A\alpha$ efferent axons) muscle fibers, the neural receptors (associated with or innervated by afferent axons) are allowed to naturally perceive and transduce the effects of such stimulation. Accordingly, methods according to the third embodiment of a method according to the present invention may be said to enhance a reduction in pain perception through muscle contraction, which may or may not be perceptible to the naked eye. It may be possible to detect the muscle contraction with electromyography (EMG) equipment. The muscle contraction, in turn, may cause natural afferent neural activity in response, thereby mediating pain relief. Electrical stimulation of efferent neural structures may or may not recruit afferent fiber activation. That is, a method according to the present invention may include a step of recruiting or activating one or more sensory, afferent axons while generating or causing a generation of an action potential in one or more motor, efferent axons. Alternatively, only efferent axons may be recruited by stimulation. For instance, when disease (e.g. diabetes or vascular insufficiency), trauma, or another disorder has impaired (or eliminated) the response of large diameter afferents (which are typically thought to respond "first"—at low levels of stimulation), electrical stimulation activation of only efferent fibers may achieve "physiological" activation of other afferents in response to the evoked extrafusal (muscle contraction) or intrafusal activity.

Indeed, the treatment of pain through efferent fiber stimulation may demonstrate at least partial dis-sensitization (e.g., partial, or complete, temporary or permanent reduction of neurological hypersensitization) of at least a portion of the nervous system through activation of afferent neural tissues that naturally respond to such stimulation. That is, it is generally recognized that the perception of pain in mammals is caused by a sensitization of afferent sensory receptors, including free nerve endings, to noxious or conventional or previously non-noxious stimuli. Sensitization is the process whereby previously non-noxious stimuli are perceived as painful, and this is an integral part of the development and maintenance of chronic pain (as opposed to the acute, healthy pain response). Such sensitization may result from non-nociceptive primary afferents (e.g. Aβ) afferents sprouting to make additional connections in the spinal cord, from the loss of inhibition in the spinal cord, and/or from central (brain) plasticity resulting from changes in functional connectivity. However, what has been demonstrated by efferent fiber stimulation for the treatment of pain is that such stimulation may actually permanently, or at least long-term, reverse the sensitization process that formed the basis for the chronic pain being treated. Dis-sensitization resulting from efferent fiber stimulation may reverse these changes through alterations in the peripheral and/or central nervous systems, including but not limited to changes in the sensitivity of peripheral sensory receptors, changes in synaptic connectivity, changes in synaptic strength, and changes in the rate and pattern of neural activity. In response to therapy according to the present invention, the firing pattern and rate of peripheral nervous system (PNS) (e.g. afferent) fibers may change, the firing pattern and rate of central nervous system (CNS) fibers may change, and/or there may be changes in both the PNS & CNS. Additionally or alternatively, there may be changes in the threshold required to active the fibers (in the PNS, CNS, &/or both PNS & CNS). Accordingly, the effects of the efferent stimulation for the treatment of pain chronologically outlast the treatment duration, and such effects may exponentially outlast the treatment duration. For example, it is common for patients that have a reduced level of pain measured, observed or reported at the end of one month after a treatment cycle, such as a three-week treatment cycle, to demonstrate the same level of pain reduction up to one year or longer after the treatment cycle has concluded. Thus, this lasting effect is thought to demonstrate dis-sensitization, and the pain reduction experienced at approximately the stimulation treatment duration after the end of the treatment cycle may be maintained for more than 17 times the treatment duration. For example, if a patient reported a pain level of 6 prior to treatment, and a pain level of 2 at a time that is about one month after a treatment cycle (such as a three-week treatment cycle), there has been demonstrated that the patient may report a pain level of 2 at a time that is about one year after the completion of the treatment cycle. In any event, at one year after treatment, if the pain level reported by the patient is less than the pain level reported prior to treatment, then at least some dis-sensitization is thought to have occurred.

Systems and Methods

Various systems may be utilized to implement the stimulation methods provided herein. The methods may be carried out in a staged progression, which may include a percutaneous and/or transcutaneous phase. The percutaneous and/or transcutaneous stimulation phase may be followed by an implanted, percutaneous, and/or transcutaneous stimulation phase. Preferred percutaneous systems may be found in U.S. patent application Ser. No. 12/462,384, published as U.S. Patent Application Publication 2010/0036445A1, which is incorporated herein by reference in its entirety, and/or U.S. patent application Ser. No. 11/595,596, published as U.S. Patent Application Publication 2007/0123952A1, which is incorporated by reference herein in its entirety, and/or U.S. patent application Ser. No. 13/095,616, which is incorporated by reference herein in its entirety. A preferred implanted system may be found in U.S. Pat. No. 7,239,918, which is incorporated herein by reference in its entirety. Another preferred percutaneous stimulation system may be found in U.S. patent application Ser. No. 12/324,044, published as U.S. Patent Application Publication 2009/0157151A1, which is incorporated herein by reference in its entirety.

Control of a stimulator and/or stimulation parameters according to the present invention may be provided by one or more external controllers. In the case of an external stimulator, the controller may be integrated with the external stimulator. In the case of an implanted stimulator, an implanted pulse generator external controller (i.e., clinical programmer) may be a remote unit that uses RF (Radio Frequency) wireless telemetry communications (rather than an inductively coupled telemetry) to control the implanted pulse generator. The external or implantable pulse generator may use passive charge recovery to generate the stimulation waveform, regulated voltage (e.g., 10 mV to 20 V), and/or regulated current (e.g., about 10 µA to about 50 mA). Passive charge recovery is one method of generating a biphasic, charge-balanced pulse as desired for tissue stimulation without severe side effects due to a DC component of the current.

The neurostimulation pulse may by monophasic, biphasic, and/or multi-phasic. In the case of the biphasic or multi-phasic pulse, the pulse may be symmetrical or asymmetrical. Its shape may be rectangular or exponential or a combination of rectangular and exponential waveforms. The pulse width of each phase may range between e.g., about 0.1 µsec. to about 1.0 sec., as non-limiting examples. The preferred neurostimulation waveform is cathodic stimulation (though anodic may work), biphasic, and asymmetrical.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from e.g., about 1 Hz to about 300 Hz, or even as high as about 20 kHz to obtain a stochastic response, and the frequency of stimulation may be constant or varying. In the case of applying stimulation with varying frequencies, the frequencies may vary in a consistent and repeatable pattern or in a random (or pseudo random) fashion or a combination of repeatable and random patterns.

In a representative embodiment, the stimulator is set to an intensity (e.g. 1-2 mA (or 0.1-40 mA, or 0.01-200 mA), 100-300 us (or 40-1000 µs, or 1-10,000 µs)) sufficient to activate the targeted efferent or afferent neural structures, using an electrode that is preferably spaced at some distance (e.g. 1 mm) away from the targeted structure. Additionally or alternatively, an electrode may be placed in direct contact with a target neural structure. If the stimulus intensity is too great, it may generate large muscle twitches or contractions sufficient to disrupt correct placement of the lead. If stimulus intensity is too low, the lead may be advanced too close to the targeted nerve of passage (beyond the optimal position), possibly leading to incorrect guidance, nerve damage, mechanically evoked sensation (e.g. pain and/or paresthesia) and/or muscle contraction, inability to activate the target nerve fiber(s) without activating non-target nerve fiber(s), improper placement, and/or improper anchoring of the lead (e.g. the lead may be too close to the neural structure and no longer able to anchor appropriately in the targeted anchoring tissue, such as muscle or adipose tissue).

In a representative embodiment, the stimulator may be set to a frequency (e.g. 0.5-12 Hz (or 0.1-20 Hz, or 0.05-40 Hz)) low enough to evoke visible muscle twitches (i.e. non-fused muscle contraction) and/or muscle contraction(s) of the targeted muscle(s) innervated by the target nerve of passage, but high enough that that the targeted nerve will be activated before the lead is advanced beyond an optimal position, preferably spaced from the nerve. An Example of preferred stimulation parameters are as follows:

| Parameter | Default | Minimum | Maximum | Adjusts in increments of |
|---|---|---|---|---|
| Amplitude | 20 mA | 1 mA | 20 mA | 1 mA |
| Frequency | 12 Hz | 5 Hz | 25 Hz | 1 Hz |
| Pulse Duration Minimum | 20 μsec | 20 μsec | 200 μsec | 10 μsec |
| Pulse Duration Maximum | Pulse Duration Minimum | Pulse Duration Minimum | 200 μsec | 10 μsec |
| Pulse Duration Normal | Pulse Duration Minimum | Pulse Duration Minimum | Pulse Duration Maximum | 10 μsec |
| Therapy Time | 6 hours | 15 min | 12 hours | 15 min |
| Duty Cycle | 50% | 50% | 50% | N/A |

To position an electrode in vivo, preferably while stimulation is being applied, the lead (non-limiting examples of the lead could include a single or multi-contact electrode that is designed for temporary (percutaneous) or long-term (implant) use or a needle electrode (used for in-office testing only)) may be advanced (e.g. slowly advanced) towards the targeted nerve until a desired indicator response (e.g. muscle twitch, muscle contraction, patient sensation, and/or some combination) is obtained, thereby defining an optimal placement position. The intensity may then be decreased (e.g. gradually decreased) as the lead is advanced (e.g. advanced slowly) closer to the targeted nerve until the desired indicator response(s) may be obtained at smaller intensity(ies) within the target range (e.g. 0.1-1.0 mA (or 0.09-39 mA, or 0.009-199 mA), 100-300 μs (or 40-1000 μs, or 1-10,000 μs)) at some distance (e.g. X2 mm, where X2<X1, and (as a non-limiting example) X1 may be multiple times larger than X2, such as X1≥2*X2, or X1≥5*X2, or X1≥20*X2) from the target nerve. If specific response(s) (e.g. desired response(s) and/or undesired response(s)) can be obtained at a range of intensities that are too low, then the lead may be located in a non-optimal location (e.g. too close to the target nerve(s)). Non-limiting examples of ranges of intensities that may be considered too low include those that are a fraction (e.g. <⅔, or <⅕, or <1/10) of the intensities that obtained the desired response(s) at X1.

The preferred stimulus intensities are a function of many variables, are meant to serve as non-limiting examples only, and may need to be scaled accordingly. As an example, if electrode shape, geometry, or surface area were to change, then the stimulus intensities may need to change appropriately. For example, if the intensities were calculated for a lead with an electrode surface area of approximately 20 mm², then they may need to be scaled down accordingly to be used with a lead with an electrode surface area of 0.2 mm² because a decrease in stimulating surface area may increase the current density, increasing the potential to activate excitable tissue (e.g. target and non-target nerve(s) and/or fiber(s)). Alternatively, if the intensities were calculated for a lead with an electrode surface area of approximately 0.2 mm², then the intensities may need to be scaled up accordingly to be used with a lead with an electrode surface area of 20 mm². Alternatively, stimulus intensities may need to be scaled to account for variations in electrode shape or geometry (between or among electrodes) to compensate for any resulting variations in current density. In a non-limiting example, the electrode contact surface area may be 0.1-20 mm², 0.01-40 mm², or 0.001-200 mm². In a non-limiting example, the electrode contact configuration may include one or more of the following characteristics: cylindrical, conical, spherical, hemispherical, circular, triangular, trapezoidal, raised (or elevated), depressed (or recessed), flat, and/or borders and/or contours that are continuous, intermittent (or interrupted), and/or undulating.

Stimulus intensities may need to be scaled to account for biological factors, including but not limited to patient body size, weight, mass, habitus, age, and/or neurological condition(s). As a non-limiting example, patients that are older, have a higher body-mass index (BMI), and/or neuropathy (e.g. due to diabetes) may need to have stimulus intensities scaled higher (or lower) accordingly.

As mentioned above, if the lead is too far away from the targeted nerve, then stimulation may be unable to evoke the desired response (e.g. muscle contraction(s), comfortable sensation(s), and/or pain relief) in the desired region(s) at the desired stimulus intensity(ies). If the lead is too close to the targeted nerve, then stimulation may be unable to evoke the desired response(s) (e.g. muscle contraction(s), comfortable sensation(s), and/or pain relief) in the desired region(s) at the desired stimulus intensity(ies) without evoking undesirable response(s) (e.g. unwanted and/or painful muscle contraction(s), sensation(s)), increase in pain, and/or generation of additional pain in related or unrelated area(s)). In some cases, it may difficult to locate the optimal lead placement (or distance from the targeted nerve) and/or it may be desirable to increase the range stimulus intensities that evoke the desired response(s) without evoking the undesired response(s) so alternative stimulus waveforms and/or combinations of leads and/or electrode contacts may be used. A non-limiting example of alternative stimulus waveforms may include the use of a pre-pulse to increase the excitability of the target fiber(s) and/or decrease the excitability of the non-target fiber(s).

Those skilled in the art will recognize that, for simplicity and clarity, the full structure and operation of all devices and processes suitable for use with the present invention is not being depicted or described herein. Instead, only so much of an implantable pulse generator and supporting hardware as is unique to the present invention or necessary for an understanding of the present invention is depicted and described. The remainder of the construction and operation of the IPGs described herein may conform to any of the various current implementations and practices known in the art.

Pain relief provided by systems and methods according to the present invention may be correlated to an analysis of quality of life of the animal receiving such relief. It may be important to measure the health-related quality of life (HRQOL), as pain is known to impact even otherwise simple, daily activities. There is a plurality of generally accepted methodologies for measuring improvements in a patient's quality of life. One methodology includes analysis of patient responses to one or more questions from an SF-36 Health Survey, available from Quality Metric, Inc., of Lincoln, R.I. The SF-36 is a generic health survey of 36 items designed to assess basic physical functioning and emotional well-being regardless of the disease or treatment. The 36 items are grouped into eight domains: physical functioning, role limitations due to physical problems, social functioning, bodily pain, general mental health, role limitations due to emotional problems, vitality, and general health perceptions. The items include questions related to the following:

present and comparative general health;

frequency and severity of physical health or emotional limitations on typical daily activities, such as stair-climbing, personal positioning such as squatting or kneeling, walking, and maintenance of personal hygiene;

amount of bodily pain and interference of such pain on daily and social activities;

comparison of general health to others; and feelings such as nervousness, peacefulness, amount of energy, depression or happiness, and exhaustion.

Generally, the ratings provided by the patient are on scales of, e.g., 1 to 3, or 1 to 5.

Another methodology of correlating treatment to quality of life involves an analysis of data from the Pain Disability Index (PDI), which is a validated survey that measures the degree to which pain disrupts activities such as work and athletics. Many patients with chronic pain believe increased ability to function physically is an important objective for pain treatment, and assessment of the impact of pain on physical functioning is recommended as one of the core outcome measures in chronic pain studies. The PDI is considered a simple and rapid tool for evaluating the impact that pain has on physical functioning. The PDI provides patient feedback related to the impact of pain on seven categories of life activity. Generally, each category is rated on a zero to ten scale, where zero indicates no disability at all in such life activity and ten indicates that a patient has been prevented from engaging in all activities of the category. The seven categories of the PDI are:

Chores and errands: This category refers to activities of related generally to home life and/or family. It includes chores or duties performed around the house (e.g., yard work, dusting, laundry) and errands or favors for other family members (e.g., driving the children to school, grocery shopping);

Leisure time: This category includes athletics, hobbies, and other similar recreation;

Social activity: This category refers to interaction with friends and acquaintances other than family members, such as attendance at parties, a theater, concerts, restaurants, and other social functions;

Job-related activities: This category refers to activities that are a part of or directly related to one's job, whether or not it is a paying, non-paying or volunteer career;

Sexual behavior: This category refers to the frequency and quality of one's sex life;

Personal maintenance: This category includes activities related to independent daily living (e.g. taking a shower, driving, getting dressed, shaving, etc.); and Life-sustaining behavior: This category refers to basic behaviors such as eating, sleeping, and breathing.

Alternatively or additionally, other validated measurements or surveys, such as the Brief Pain Inventory-Short Form (BPI-SF) or Brief Pain Inventory-Long Form (BPI-LF), may be used. For instance, BPI-SF (or -LF) question number 3 requests that patients rate the worst pain they have experienced in the past week on a scale from zero to ten, where zero indicates "no pain" and ten indicates "pain as bad as you can imagine." Alternatively or additionally, BPI-SF question 9 requests that patients rate, on a scale of zero to ten, the interference of pain on various activities. A rating of zero indicates that pain has no interference on the activity and a rating of ten indicates that pain completely interferes with such activity. Such survey may include ratings of interference on activities such as general activity, walking ability, normal work (inside and outside the home), sleep, and interpersonal relations. Further such survey may include ratings of personal feelings, such as the pain interference with mood or enjoyment of life. Where all seven eleven-point-scale ratings are included, a mean score between zero and ten may be calculated by summing the seven ratings and dividing by seven.

The quality of life surveys are preferably administered both before and after a treatment period, and the results thereof are compared. For instance, if the BPI-SF (or -LF) question 9 is used, a comparison of the post-treatment mean and the pre-treatment mean may indicate a level of success of the treatment. As used herein, post-treatment may refer to any time after the start of treatment, including but not limited to after completion of a treatment period, duration, regime, or protocol. On the eleven-point (0-10) mean scale of the BPI-SF question 9, it is preferable to have an improvement (reduction) of more than one point out of the total ten possible points, more preferably to have an improvement of more than two points, and most preferred to have an improvement of more than three points. After any mid- or post-treatment quality of life analysis, stimulation parameters or methodologies may be altered, and the quality of life may again be examined, and compared to baseline (prior to receipt of any treatment) and/or to other post-treatment results to determine whether the altered parameters were any more or less effective than the first in improving quality of life.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

Having thus described the invention, we claim:

1. A method of reducing a perception of pain, the method comprising:

percutaneously inserting an electrode in-vivo a therapeutically effective distance from a target afferent nerve fiber; and electrically stimulating through the electrode the target afferent nerve fiber at a frequency of about 4 kHz to about 20 kHz preventing stimulation-induced pain while generating a desired response in the target afferent nerve fiber to cause pain relief while avoiding generation of an unwanted response in a non-target nerve fiber.

2. The method of claim 1, wherein electrically stimulating through the electrode the target afferent nerve fiber does not cause nerve damage or paresthesia.

3. The method of claim 1, wherein the therapeutically effective distance is 1 mm.

4. The method of claim 1, wherein the unwanted response in the non-target nerve fiber comprises painful muscle contraction or painful sensation.

5. A method of reducing a perception of pain, the method comprising:

percutaneously inserting an electrode in-vivo a therapeutically effective distance from a target afferent nerve fiber; and electrically stimulating through the electrode the target afferent nerve fiber with a high frequency stimulation of about 4 kHz to about 20 kHz to generate a desired response in the target afferent nerve fiber while avoiding generation of unwanted responses in a non-target nerve fiber.

6. The method of claim 5, wherein the desired response is pain relief.

7. The method of claim 5, wherein the high frequency stimulation is a modulated high frequency stimulation.

8. The method of claim 7, wherein electrically stimulating through the electrode the target afferent nerve fiber with a modulated high frequency stimulation does not produce nerve damage, pain, or paresthesia.

9. A method of claim 5, wherein the therapeutically effective distance from a target afferent nerve fiber is 1 mm.

10. A method of reducing a perception of pain comprising:
applying high frequency electrical stimulation of about 4 kHz to about 20 kHz to at least a portion of a peripheral nervous system through an electrode inserted percutaneously and spaced at a distance at least 1 mm away from a targeted nerve structure to generate a stochastic response of action potentials in a plurality of target afferent sensory nerve fibers while avoiding action potentials in non-target small sensory afferent nerve fibers causing a reduction of perception of pain.

11. The method of claim 10, wherein applying high frequency electrical stimulation does not produce nerve damage, pain, or paresthesia.

12. A system to reduce a perception of pain comprising:
an electrode percutaneously inserted in-vivo;
an electrical pulse generator applying electrical stimulation to at least a portion of a peripheral nervous system through the electrode at a frequency of about 4 kHz to about 20 kHz generating a desired response and preventing stimulation-induced pain in at least one target afferent sensory nerve fiber while avoiding action potentials in non-target small sensory afferent nerve fibers causing a reduction of perception of pain.

13. The system of claim 12, wherein the high frequency electrical stimulation does not produce nerve damage, pain, or paresthesia.

14. The system of claim 12, wherein the electrode is percutaneously inserted a therapeutically effective distance from the at least one target afferent sensory nerve fiber.

15. The system of claim 14, wherein the therapeutically effective distance is 1 mm.

* * * * *